United States Patent
Fuchs et al.

(10) Patent No.: US 9,976,173 B2
(45) Date of Patent: May 22, 2018

(54) DEVICES, COMPOSITIONS AND METHODS PERTAINING TO MICROSCOPIC ANALYSIS OF MICROORGANISMS AND OTHER ANALYTES OF INTEREST

(71) Applicant: AdvanDx, Inc., Woburn, MA (US)

(72) Inventors: Martin Fuchs, Uxbridge, MA (US); Michelle C. Meltzer, Chelmsford, MA (US); Melissa K Deck, Somerville, MA (US)

(73) Assignee: ADVANDX, INC., Woburn, MA (US)

( * ) Notice: Subject to any disclaimer, the term of this patent is extended or adjusted under 35 U.S.C. 154(b) by 0 days. days.

(21) Appl. No.: 14/434,759

(22) PCT Filed: Oct. 9, 2013

(86) PCT No.: PCT/US2013/064120
§ 371 (c)(1),
(2) Date: Apr. 9, 2015

(87) PCT Pub. No.: WO2014/059011
PCT Pub. Date: Apr. 17, 2014

(65) Prior Publication Data
US 2015/0275280 A1 Oct. 1, 2015

Related U.S. Application Data

(60) Provisional application No. 61/711,690, filed on Oct. 9, 2012.

(51) Int. Cl.
*C12Q 1/68* (2018.01)
*C12M 1/34* (2006.01)

(52) U.S. Cl.
CPC .......... *C12Q 1/6827* (2013.01); *C12Q 1/689* (2013.01); *C12Q 1/6834* (2013.01); *C12Q 1/6841* (2013.01); *C12Q 1/6895* (2013.01); *C12Q 1/6837* (2013.01); *C12Q 1/6888* (2013.01)

(58) Field of Classification Search
None
See application file for complete search history.

(56) References Cited

U.S. PATENT DOCUMENTS

| | | |
|---|---|---|
| 3,963,442 A | 6/1976 | Bullard et al. |
| 4,038,485 A | 7/1977 | Johnston et al. |
| 4,219,334 A | 8/1980 | Schluter et al. |
| 4,959,305 A | 9/1990 | Woodrum |
| 5,246,664 A | 9/1993 | Nagata et al. |
| 5,397,711 A | 3/1995 | Finckh |
| 5,403,706 A | 4/1995 | Wilk et al. |
| 5,616,478 A | 4/1997 | Chetverin et al. |
| 5,726,064 A | 3/1998 | Robinson et al. |
| 5,958,698 A | 9/1999 | Chetverin et al. |
| 6,045,753 A | 4/2000 | Loewy et al. |
| 6,228,982 B1 | 5/2001 | Norden et al. |
| 6,309,893 B1 | 10/2001 | Deeley et al. |
| 6,355,421 B1 | 3/2002 | Coull et al. |
| 6,361,942 B1 | 3/2002 | Coull et al. |
| 6,607,889 B1 | 8/2003 | Coull et al. |
| 6,649,349 B2 | 11/2003 | Gildea et al. |
| 6,790,613 B1 | 9/2004 | Shi et al. |
| 6,905,824 B2 | 6/2005 | Rigby et al. |
| 7,598,036 B2 | 10/2009 | Chu |
| 7,816,501 B2 | 10/2010 | Coull et al. |
| 2001/0010910 A1 | 8/2001 | Hyldig-Nielsen et al. |
| 2003/0091988 A1 | 5/2003 | Johansen et al. |
| 2003/0129611 A1 | 7/2003 | Bao et al. |
| 2003/0148277 A1 | 8/2003 | Chiesa et al. |
| 2004/0253613 A1 | 12/2004 | Taylor et al. |
| 2005/0032091 A1 | 2/2005 | Stender et al. |
| 2009/0105082 A1* | 4/2009 | Chetverin ............ C12Q 1/6818 506/7 |
| 2009/0325263 A1 | 12/2009 | Ponaka et al. |

(Continued)

FOREIGN PATENT DOCUMENTS

| | | |
|---|---|---|
| EP | 1806584 A1 | 7/2007 |
| WO | 2000/034521 A1 | 6/2000 |

(Continued)

OTHER PUBLICATIONS

Rupcich et al Anal. Chem. 2005. 77: 4300-4307.*
Fiorini Biotechniques. 2005. 38: 429-446.*
Dodge et al Anal Chem. 2004. 76: 1778-1787.*
Braasch and Corey, "Synthesis, Analysis, Purification and Intracellular Delivery of Peptide Nucleic Acids," Methods, 23:97-107 (2001).
Chetverina et al., "Molecular Colony Diagnostics: Detection and Quantitation of Viral Nucleic Acids by In-Gel PCR," BioTechniques, 33:150-156 (2002).
Chetverina et al., "Simultaneous assay of DNA and RNA targets in the whole blood using novel isolation procedure and molecular colony amplification," Analyt. Biochem., 334:376-381 (2004).
Discussion of "The Sol-Gel Process" at Aerogel.org, url: http://www.aerogel.org/?p=992[Feb. 17, 2014 8:27:39 AM] (downloaded on Feb. 17, 2014).

(Continued)

*Primary Examiner* — Carla J Myers
(74) *Attorney, Agent, or Firm* — McCarter & English, LLP; Jonathan M. Sparks

(57) ABSTRACT

This invention pertains to devices, compositions and methods that can be used for the rapid determination of microorganisms, cells and other analytes of interest (e.g. a nucleic acid target) as well as associated properties of said microorganisms, cells and analytes. For example, said devices, compositions and/or methods can be applied to the determination of a trait of a microorganism present in a sample. Said devices, compositions and methods utilize matrix-forming prolonged-dissolution hydrophilic polymer to encapsulate hybridization probes and optionally other assay reagents within two or more reagent zones and/or matrix zones disposed on the surface of a substrate. Each reagent zone and/or matrix zone can be designed as a separate assay. Thus, a plurality of assays can be performed on a single substrate. In some embodiments, devices can be supplied in a form ready for a customer to rapidly perform one or a plurality of assays.

34 Claims, 4 Drawing Sheets

(56) References Cited

U.S. PATENT DOCUMENTS

2010/0209927 A1* 8/2010 Menon .................. B01L 3/5027
435/6.16
2010/0211158 A1 8/2010 Haverty et al.

FOREIGN PATENT DOCUMENTS

WO 2005/090610 A2 9/2005
WO 2008/072209 A2 6/2008

OTHER PUBLICATIONS

Huang et al., "A gel-based solid-phase amplification and its application for SNP typing and sequencing on-chip," Analyst, (Web publication: Oct. 5, 2009).
International Search Report issued in PCT/US2013/064120 dated Jan. 31, 2014.
Mitra and Church, "In situ localized amplification and contact replication of many individual DNA molecules," Nucl. Acids Res., 27(24):e34, 6 pages (1999).
Nielsen, "Methods in Molecular Biology," vol. 208; Peptide Nucleic Acids, Protocols and Methods, Humana Press, Totowa, NJ (2002).
Nutiu and Li, "Structure-Switching Signaling Aptamers," JACS, 125(16):4771-4778 (2003).
Ortiz et al., "PNA molecular beacons for rapid detection of PCR amplicons," Molec. Cell. Probes, 12:219-226 (1998).
Rupcich et al., "Entrapment of Fluorescent Signaling DNA Aptamers in Sol-Gel Derived Silica," Anal. Chem., 77:4300-4307 (2005).
Samatov et al. "Real-time monitoring of DNA colonies growing in a polyacrylamide gel," Analyt. Biochem., 356:300-302 (2006).
Shen et al., "Entrapment of Fluorescence Signaling DNA Enzymes in Sol-Gel Materials for Metal Ion Sensing," Anal. Chem., 79:3494-3503 (2007).
Søgaard et al., "Direct Identification of Major Blood Culture Pathogens, Including Pseudomonas aeruginosa and *Esherichia coli*, by a Panel of Fluorescence in Situ Hybridization Assays Using Peptide Nucleic Acid Probes," J. Clin. Micro., 43(4):1947-1949 (2005).
Tackett et al., "Non-Watson-Crick interactions between PNA and DNA inhibit the ATPase activity of bacteriophage T4 Dda helicase," Nucleic Acids Res., 30:950-957(2002).
Uhrich et al., "Polymeric Systems for Controlled Drug Release," Chem. Rev., 99:3181-3198 (1999).
Varshosaz and Koopaie, "Cross-linked Poly(vinyl alcohol) Hydrogel: Study of Swelling and Drug Release Behavior," Iranian Polymer Journal, 11:123-131 (2002).
Vilaivan et al., "Hybridization of Pyrrolidinyl Peptide Nucleic Acids and DNA: Selectivity, Base-Pairing Specificity and Direction of Binding," Organic Letters, 8(9):1897-1900 (2006).
Wengel et al., "Chemistry of Locked Nucleic Acids (LNA)," Peptide Nucleic Acids, Morpholinos and Related Antisense Biomolecules, Chapter 7, pp. 114-132, (2006).
Written Opinion of the International Searching Authority issued in PCT/US2013/064120 dated Apr. 14, 2015.

* cited by examiner

DEVICES, COMPOSITIONS AND METHODS PERTAINING TO MICROSCOPIC ANALYSIS OF MICROORGANISMS AND OTHER ANALYTES OF INTEREST

CROSS REFERENCE TO RELATED APPLICATIONS

This application is a 35 U.S.C. § 371 National Phase Entry Application of International Application No. PCT/US2013/064120 filed Oct. 9, 2013, which designates the US, and which claims benefit under 35 U.S.C. § 119(e) of U.S. Provisional Application No. 61/711,690, filed Oct. 9, 2012, the contents of each are incorporated herein by reference in their entirety.

The section headings used herein are for organizational purposes only and should not be construed as limiting the subject matter described in any way.

BRIEF DESCRIPTION OF DRAWINGS

The skilled artisan will understand that the drawings, described below, are for illustration purposes only. The drawings are not intended to limit the scope of the present teaching in any way.

In the drawings, the sizes and relative positions of elements in the drawings are not necessarily drawn to scale. For example, the shapes of various elements and angles may not be drawn to scale, and some of these elements are arbitrarily enlarged and positioned to improve drawing legibility. Further, the particular shapes of the elements as drawn may not be intended to convey any information regarding the actual shape of the particular elements, and may have been selected solely for ease of recognition in the drawings.

FIG. 1 illustrates an embodiment of an assay device, wherein

FIG. 2 illustrates an embodiment of an assay device, wherein

FIG. 3 illustrates an embodiment of an assay device, wherein

FIG. 4 illustrates an embodiment of an assay device, wherein

Figure 1A:
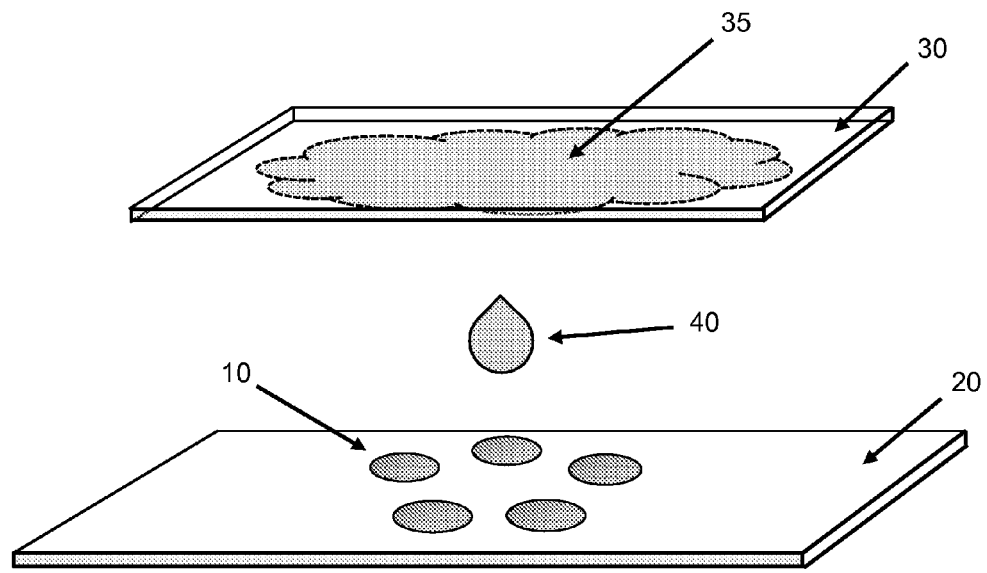
FIG. 1A illustrates the individual components of said assay and FIG. 1B illustrates the components as assembled to perform the assay.

All literature and similar materials cited in this application, including but not limited to patents, patent applications, articles, books and treatises, regardless of the format of such literature or similar material, are expressly incorporated by reference herein in their entirety for any and all purposes.

DESCRIPTION

1. Field

This invention pertains to the field of microorganism and other cell analysis as well as the determination of target sequences in a sample.

2. Introduction

Microorganism analysis can be performed by many methods. In clinical applications, the rapid determination of clinically relevant microorganisms and their associated traits is critical to delivering high quality patient care and effective treatment of infections. In particular, assays able to determine a panel of multiple microorganisms in parallel can save time and effort in the laboratory but these are only gradually being introduced because of the challenges in creating them. Moreover, studies have shown that reducing the analysis time allows antimicrobial treatment to be optimized sooner, improving patient outcomes. Therefore, it is desirable to create assays with a time to result that is as short as possible. It can also be a benefit if the assay can be performed in a simple manner using traditional laboratory equipment and methodologies. The devices, compositions and methods disclosed herein represent an advancement that addresses many of the aforementioned goals and shortcomings associated with microorganism determination. Furthermore, the devices, compositions and methods disclosed herein can also be applied to other areas of microbiology and to areas outside of microorganism determination such as to the general determination of analytes (i.e. target sequences) in a sample of interest, as for example in mammalian cells in biological research and in diagnostics (e.g. oncology).

3. Definitions

For the purposes of interpreting this specification, the following definitions will apply and whenever appropriate, terms used in the singular will also include the plural and vice versa. In the event that any definition set forth below conflicts with the usage of that word in any other document, the definition set forth below shall always control for purposes of interpreting the scope and intent of this specification and its associated claims. Notwithstanding the foregoing, the scope and meaning of any document incorporated herein by reference should not be altered by the definition presented below. Rather, said incorporated document should be interpreted as it would be by the ordinary practitioner based on its content and disclosure with reference to the content of the description provided herein.

The use of "or" means "and/or" unless stated otherwise or where the use of "and/or" is clearly inappropriate. The use of "a" means "one or more" unless stated otherwise or where the use of "one or more" is clearly inappropriate. The use of "comprise," "comprises," "comprising", "include", "includes", and "including" are interchangeable and not intended to be limiting. Furthermore, where the description of one or more embodiments uses the term "comprising", those skilled in the art would understand that in some specific instances, the embodiment or embodiments can be alternatively described using language "consisting essentially of" and/or "consisting of".

As used herein the term "analyte" refers to a target sequence undergoing analysis in, or to be analyzed by, a specific assay.

As used herein, the term "buffer" refers to a substance, or mixture of substances, that in solution tends to stabilize the hydrogen-ion concentration by neutralizing, within limits, both acids and bases.

As used herein, "chimera" refers to an oligomer comprising subunits of two or more different classes of subunits. For example, a chimera can comprise subunits of deoxyribonucleic acid (DNA) and locked nucleic acid (LNA), can comprise subunits of DNA and ribonucleic acid (RNA), can comprise subunits of DNA and peptide nucleic acid (PNA), can comprise subunits of DNA, LNA and PNA or can comprise subunits of RNA and LNA, etc. It is to be understood that what the literature refers to as LNA probes are typically chimeras (according to this definition), since said "LNA probes" usually incorporate only one or a few LNA nucleotides into an oligomer. The remaining nucleotides are typically standard DNA or RNA nucleotides.

As used herein, "determining" refers to making a decision based on investigation, data, reasoning and/or calculation. Some examples of determining include detecting, identifying and/or locating (microorganisms or other cells and/or traits) as appropriate based on the context/usage of the term herein.

As used herein the term "detergent" refers any of a class of agents, characterized by a hydrophilic polar head group attached to a nonpolar hydrocarbon chain, which can reduce the surface tension of water, emulsify, and aid in the solubilization of organic compounds and materials in an aqueous solution.

As used herein the term "disposed" refers to having been put in place.

As used herein the phrase "flat or substantially flat" refers to having a relatively smooth and even surface wherein major elements of said surface are essentially parallel and in the same plane and distinctly greater in size and number than minor non-parallel elements of said surfaces.

As used herein the term "gel" refers to a colloid in which a disperse phase has combined with the dispersion medium to produce a semi-rigid material.

As used herein the term "label" refers to a structural unit (or structural units as the case may be) of a composition (e.g. a hybridization probe) that renders the composition detectable by instrument and/or method. Non-limiting examples of labels include fluorophores, chromophores, haptens, radioisotopes and quantum dots. In some embodiments, two or more of the foregoing can be used in combination to render the composition detectable or independently (uniquely) detectable. Some words that are synonymous (i.e. interchangeable) with "label" are "detectable moiety", "tag" and "marker".

As used herein the term "matrix" refers to a surrounding substance within which something else is contained, enclosed, embedded or encapsulated.

As used herein the term "matrix film" refers to a layer of matrix coated on a surface. The layer of matrix may be coated in a thin layer on the surface. For example the matrix film can be a film of matrix with a thickness of less than 1 millimeter (mm).

As used herein the phrase "matrix-forming" refers to being capable of forming a matrix.

As used herein, the phrase "matrix zone" refers to unique location, portion or sector of a surface on which a matrix has formed or exists.

As used herein, the phrase "narrow gap" refers to a distance or gap of no more than 1 mm between two surfaces. The "gap" may be hollow (contain gas or air), may comprise matter (such as a liquid, solid or mixture of liquid and solids) or may contain alternating hollow and matter filled regions.

As used herein, "nucleic acid" refers to a nucleobase containing polymer formed from nucleotide subunits composed of a nucleobase, a ribose or 2'-deoxyribose sugar and a phosphate group. Some examples of nucleic acid are DNA and RNA.

As used herein the phrase "nucleic acid analog" refers to a nucleobase containing polymer formed from subunits wherein the subunits comprise a nucleobase and a sugar moiety that is not ribose or 2'-deoxyribose and/or a linkage (between the sugar units) that is not a phosphate group. A non-limiting example of a nucleic acid analog is a locked nucleic acid (LNA: See for example, U.S. Pat. Nos. 6,043, 060, 7,053,199, 7,217,805 and 7,427,672). See: Janson and During, "Peptide Nucleic Acids, Morpholinos and Related Antisense Biomolecules", Chapter 7, "Chemistry of Locked Nucleic Acids (LNA)", Springer Science & Business, 2006 for a summary of the chemistry of LNA.

As used herein the phrase "nucleic acid mimic" refers to a nucleobase containing polymer formed from subunits that comprise a nucleobase and a backbone structure that is not a sugar moiety (or that comprises a sugar moiety) but that can nevertheless sequence specifically bind to a nucleic acid. An example of a nucleic acid mimic is peptide nucleic acid (PNA: See for example, U.S. Pat. Nos. 5,539,082, 5,527, 675, 5,623,049, 5,714,331, 5,718,262, 5,736,336, 5,773,571, 5,766,855, 5,786,461, 5,837,459, 5,891,625, 5,972,610, 5,986,053, 6,107,470, WO92/20702 and WO92/20703). Another example of a nucleic acid mimic is a morpholino oligomer. (See Janson and During, "Peptide Nucleic Acids, Morpholinos and Related Antisense Biomolecules", Chapter 6, "Morpholinos and PNAs Compared", Springer Science & Business, 2006 for a discussion of the differences between PNAs and morpholinos. A further example of a nucleic acid mimic is the pyrrolidinyl polyamide (PP). A PP is an oligomeric polymer comprising a nucleobase and polyamide backbone as described in U.S. Pat. Nos. 6,403,763, 6,713, 603, 6,716,961 and 7,098,321 as well as Vilaivan et al., "*Hybridization of Pyrrolidinyl Peptide Nucleic Acids and DNA: Selectivity, Base-Pairing Specificity and Direction of Binding*", Organic Letters, 8(9): 1897-1900 (2006).

As used herein the term "nucleobase" refers to those naturally occurring and those non-naturally occurring heterocyclic moieties commonly known to those who generate polymers that can sequence specifically bind to nucleic acids. Non-limiting examples of suitable nucleobases include: adenine, cytosine, guanine, thymine, uracil, 5-propynyl-uracil, 2-thio-5-propynyl-uracil, 5-methylcytosine, pseudoisocytosine, 2-thiouracil and 2-thiothymine, 2-aminopurine, N9-(2-amino-6-chloropurine), N9-(2,6-diaminopurine), hypoxanthine, N9-(7-deaza-guanine), N9-(7-deaza-8-aza-guanine) and N8-(7-deaza-8-aza-adenine).

As used herein the phrase "on the surface" of a substrate is not intended to imply that whatever is 'on the surface' makes direct physical contact with said surface. Rather, to say that a substance is 'on the surface' refers to the substance being directly or indirectly (e.g. by contacting an intervening layer of material that is in direct contact with said surface of said substrate) in contact with said surface.

As used herein the term "probe" or the phrase "hybridization probe" refers to a composition that binds to a select target sequence by hybridization. Non-limiting examples of polymers that can be used as probes include nucleic acid oligomers, (e.g. DNA, RNA, etc.) nucleic acid analog oligomers (e.g. locked nucleic acid (LNA)), nucleic acid mimic oligomers (e.g. peptide nucleic acid (PNA)) and chimeras).

As used herein the phrase "prolonged-dissolution hydrophilic polymer" refers to a substance that can be added to a aqueous solution such that: (i) when said aqueous solution containing said substance is applied to a substrate and the aqueous solution is permitted to evaporate it produces a matrix that embeds or encapsulates other component of the aqueous solution; and (ii) when solvent is thereafter added to said matrix, said matrix resolvates over a short period of time (e.g. 30 seconds to 10 minutes) as a result of the slow rehydration of said substance. Examples of said "prolonged-dissolution hydrophilic polymer" include: multi-subunit sugar copolymers, pullulan, methyl cellulose, carboxymethyl cellulose, carboxyethyl cellulose, carboxypropyl cellulose, hydroxyethyl cellulose, hydroxypropyl cellulose hydroxypropyl methyl cellulose, polyvinylalcohols, polyvinylpyrrolidones, polyacrylamides, polyacrylic acids, polyethyleneimines, pectins or mixtures of any two or more of the forgoing.

As used herein, the phrase "reagent zone" refers to unique location, portion or sector of a matrix film in which one or more hybridization probes (and optionally other reagents) is disposed.

As used herein the phrase "residual water" refers to water molecules remaining in a matrix created by evaporation of an aqueous solvent from a solution comprising a 'prolonged-dissolution hydrophilic polymer'; it being understood that the evaporation process may not completely remove all water molecules from the solution of polymer.

As used herein the term "sample" refers to a test sample.

As used herein, the term "semi-solid" refers to having a viscosity and rigidity intermediate between that of a solid and a liquid. A semi-solid exhibits some properties of: 1) liquids, such as shape conformity to something applying pressure to it, or the ability to flow under pressure; and 2) properties of solids such as the ability to support its weight.

As used herein the term "substrate" refers to a base material. Substrates used in the practice of this invention can be transparent materials such as glass or transparent polymer materials.

As used herein the term "surface" refers to the boundary or interface of a substrate.

As used herein the term "target" or phrase "target sequence" are interchangeable and refer to a nucleic acid molecule to which a hybridization probe is designed to hybridize with specificity to thereby confirm a condition of interest in a sample of interest being examined in a particular assay.

As used herein the term "trait" refers to any characteristic or property of a microorganism or other cell that can be determined by analysis of the chromosomal DNA, mRNA and/or native plasmid DNA of said microorganism. An example of one such trait is methicillin-resistance in *Staphylococcus aureus*. Said trait is dependent on the presence of the mecA gene (i.e. the chromosomal DNA) and expression of said gene (e.g. by production of mRNA from said gene).

As used herein the term "transparent" refers to a property of a material (e.g. a substrate) whereby said material permits transmission of at least 65% of any visible, fluorescent or infrared light directed to one side (or surface) of said material through to the other side (or surface) of said material.

4. General

It is to be understood that the discussion set forth below in this "General" section can pertain to some, or to all, of the various embodiments of the invention described herein.

A. Substrate

A substrate is a base material comprising a surface on which one or more matrix zones, matrix films and/or reagent zones can be disposed and/or formed. The assays and devices used in embodiments of this invention can utilize more than one substrate. In principle, said surfaces of said substrates can be used to immobilize and/or store reagents, probes, samples and other assay components, some or all of which may be embedded or encapsulated in a matrix. Assays can be performed on the surface of a substrate. Generally the substrate provides a working/storage surface but is otherwise generally inert with respect to the practice of various assays that are some embodiments of this invention.

The substrate can be made from just about any material that forms a solid surface. Generally, the substrate is formed using a material that generates a non-porous surface but that is not an absolute requirement. In some embodiments, the substrate or substrates can be transparent. Some non-limiting examples of materials that can be used to form a substrate include: 1) glass; 2) polymeric materials (i.e. plastics) such as polystyrenes, polyimides, polycarbonates, polyacrylics, polyacrylates and polymethacrylates (e.g. poly (methyl methacrylate), cyclic polyolefins and combinations of any two or more of the said polymers; and 3) metals such as gold, silver, aluminum, inconel (e.g. Inconel Alloy 625) and stainless steel. As noted above, the material selected as a substrate should normally be selected to be inert with respect to the various probes, polymers and other reagents used in a particular assay.

Substrates used in practice of this invention generally are flat or substantially flat. There is no requirement that the surfaces contain wells, impressions or other physical barriers (to the free flow of a liquid) included in their design that would segregate one matrix zone or reagent zone from any of the other matrix zones or reagent zone or otherwise impede the free flow of a liquid over a surface of a substrate. Consequently, this invention can be practiced, inter alia, with many off-the-shelf products such as a conventional glass microscope slide. Thus, this invention lends itself to practice using traditional laboratory equipment and methodologies.

B. Matrix, Matrix Zones & Reagent Zones

Applicants have observed that they can prepare and store probes and other reagents in an assay-ready format by embedding or encapsulating them in a matrix formed using a matrix-forming prolonged-dissolution hydrophilic polymer. It is an advantage that device component parts and assay devices (as described below) can be manufactured in bulk and stored for periods of time before being used by laboratory personnel.

It is not a requirement that all of the various probes and reagents needed for a particular test or assay be embedded or encapsulated in the matrix. However, it is advantageous to be able to prepare substrates comprising a plurality of matrix zones and/or reagent zones disposed thereon in a pre-defined arrangement wherein various probes and other reagents present at each matrix zone or reagent zone can be independently selected to perform a defined assay or test. In this way, the substrate comprising the plurality of matrix zones or reagent zones can be brought into contact with a sample to thereby perform a plurality of assays/tests on said sample.

Each matrix is formed using a matrix-forming prolonged-dissolution hydrophilic polymer. Examples of said "prolonged-dissolution hydrophilic polymer" include (but are not limited to): multi-subunit sugar copolymers, pullulan, methyl cellulose, carboxymethyl cellulose, carboxyethyl cellulose, carboxypropyl cellulose, hydroxyethyl cellulose, hydroxypropyl cellulose hydroxypropyl methyl cellulose, polyvinylalcohol(s), polyvinylpyrrolidones(s), polyacrylamide(s), polyacrylic acid(s), polyethyleneimines(s), pectin(s) or mixtures of any two or more of the forgoing. Some preferred polymers are polyvinyl alcohol (PVA), Pullulan (a maltotriose oligomer) and hydroxypropyl methyl cellulose.

A matrix-forming prolonged-dissolution hydrophilic polymer is characterized by its somewhat sluggish rehydration when a prepared matrix is exposed to an aqueous liquid. By delay in rehydration we mean that rehydration can take place on the order of from about ten (10) seconds to about ten (10) minutes depending on the polymer selected, the makeup of the aqueous liquid used to rehydrate the polymer and general state of the matrix prior to attempted rehydration (e.g. is it a gel or a hard solid). It is also a common property, but not necessarily a requirement, that the matrix-forming prolonged-dissolution hydrophilic polymer form solutions of high viscosity. It seems that for many applications, the preferred matrix-forming prolonged-dissolution hydrophilic polymers are linear polymers. The matrix-forming prolonged-dissolution hydrophilic polymers may be selected for a particular test/assay for other attributes associated with the polymer. For example polyvinyl alcohol and pullulan are non-hygroscopic while cellulose derivatives tend to be hygroscopic. Polyvinyl alcohol also appears to be an effective barrier to oxygen. This property may prove beneficial in the practice of some methods of this invention.

Generally the matrix is prepared by mixing the matrix-forming prolonged-dissolution hydrophilic polymer with an aqueous solvent (i.e. aqueous liquid that may optionally contain organic polar solvents such as methanol, ethanol, propanol, isopropanol or acetonitrile) as well as the probes and/or other reagents to be deposited at a matrix zone to or reagent zone thereby generate a matrix solution. A matrix solution can be prepared for each of the plurality of assays/tests to be performed on said substrate. Each different matrix solution can then be disposed at a defined location on said substrate and then the aqueous solvent can be evaporated to form a matrix zone. Alternatively, the matrix solution (which may contain only one or more select regents and may not include one or more of the hybridization probes needed for an assay at a reagent zone) can be applied to a substrate to form a coating. Evaporation of the solvent generates a film sometimes referred to herein as a matrix film or film of matrix. Reagent zones within said matrix film can then be created at defined areas/locations by depositing one or more probes and optionally other reagents that are unique to the assay to be performed at each reagent zone.

Regardless, when dried by evaporation of said solvent, the matrix applied to the substrate does not flow. Depending on the exact formulation, the dried matrix will comprise probes and/or reagents substantially homogeneously disposed therein. In this form, the matrix can be referred to as a gel, semi-solid or solid. Once all the matrix zones or reagent zones are prepared, the substrate can be used to examine a sample of interest for the plurality of assays/tests to be performed.

More particularly, in some embodiments, reagents can be disposed as zones within a film of matrix to thereby form a 'reagent zone'. A substrate with reagent zones contained in a matrix film can be prepared in the following manner. The matrix is prepared as described above by mixing the matrix-forming prolonged-dissolution hydrophilic polymer with an aqueous solvent (i.e. aqueous liquid). The matrix solution is then applied to the substrate in a thin layer by spin coating. Spin coating is widely used in the semiconductor industry to form thin films of photoresist on semiconductor wafers. The liquid photoresist is applied to the spinning wafer and spread into a thin film by the action of the rotation combined with the evaporation of the solvent. The applicants have found that thin films of prolonged-dissolution polymer can be prepared by applying matrix solution to the substrate and then spinning the substrate to distribute the fluid into a thin film. Once the film is created, reagent zones can be formed within the film by dispensing reagent solution to defined locations on the film before the film has completely dried. The reagent diffuses into the film and becomes trapped therein when the film dries. This creates reagent zones within the film at each of the defined locations. With reagent zones created in this way, the substrate can be used to examine a sample of interest for the plurality of assays/tests to be performed. The foregoing is provided by way of example. It is to be understood that it is not a requirement that the reagents unique to a reagent zone be applied before the film has completely dried. Rather, this is merely one option of a plurality of options.

C. Hybridization Probes

Hybridization probes used in the practice of this invention can be selected to determine a microorganism, cell, trait, analyte or other condition of interest in an assay. The success of such a probe with respect to the determination of a microorganism, cell, trait, analyte or other condition of interest in an assay is dependent upon its nucleobase sequence and associated hybridization properties. Determination of the microorganism, cell, trait, analyte or other condition of interest in an assay is made possible by determining hybridization of said probe to its complementary target sequence which target sequence is selected because it is known to be uniquely correlated with the presence of said microorganism, cell, trait, analyte or other condition of interest or because its hybridization to its complementary target, in combination with the hybridization of one or more other probes to their complementary targets in the same microorganism uniquely correlates with the presence of said microorganism, cell, trait, analyte or other condition of interest.

A single probe can be used in some assays while combinations of probes are used in other assays. Generally speaking, practice of this invention involves one assay per matrix zone or reagent zone. Some or all of the probes used for an assay can be embedded or encapsulated in a matrix zone or reagent zone. If some of the probes are not sequestered in the matrix zone or reagent zone, they can be added, for example, as a component of the aqueous solvent (e.g. rehydration fluid) used to rehydrate the matrix at the time an assay is to be performed. In some embodiments, they can be independently added to the assay.

In some embodiments, the probes are selected based on their interaction with other probes in the assay rather than with the target sequence. For example, in several embodiments of this invention, at least one hybridization probe comprising a linked fluorescent label is combined with at least one hybridization probe comprising a linked quencher moiety. When combined in an assay, these probes are typically designed to interact with each other when at least one of them is not interacting with a target sequence. In this way, when not interacting with a target sequence, the two probes hybridize to each other such that the fluorophore of one probe interacts with the quencher of the other probe to thereby neutralize the fluorescent signal. Generally, such probes used in these assay formats are designed such that if the target sequence is present, the probe designed to hybridize to the target sequence forms a more stable hybrid such that formation of the probe/target hybrid is more energetically favored as compared to the probe/probe hybrid. More information regarding the description and use of probes (referred to as 'detection complexes') of this type can be found in U.S. Pat. No. 6,361,942 to Coull et al., in U.S. Pat. No. 6,607,889 to Coull et al. and in U.S. Pat. No. 6,905,824 to Rigby et al. In general, these 'detection complexes', although comprised of two or more probes, are considered to be a single probe directed to determining a single target sequence in the assay/sample.

D. Aqueous Solvent

In embodiment of this invention, an aqueous solvent is placed in contact with matrix zones present on the surface of the substrate. This aqueous solvent is sometimes referred to as a rehydration fluid or rehydration buffer. Typically contact between the aqueous solvent and the matrix zone occurs by disposing the aqueous solvent on said surface. Because the surface can be flat or substantially flat (and without any physical barriers to free flow of the solvent), disposing the aqueous solvent on the surface typically results in rapid flow and the establishment of contact between the aqueous solvent and the plurality of matrix zones disposed on the surface of the substrate. Without the presence of the matrix-forming prolonged-dissolution hydrophilic polymer in the reagent zones, the initially rapid flow would cause deleterious transport and mixing of the deposited reagents. Instead, the aqueous solvent rehydrates the matrix-forming prolonged-dissolution hydrophilic polymer in a delayed manner thereby releasing probes and other reagents sequestered therein only after the initial flow has ceased (or substantially ceased) and the aqueous solvent has reached a static or substantially static condition thereby allowing them to mix with and optionally react with other components of the aqueous solvent and or a sample in a localized region of the surface of the substrate. Indeed, in some embodiments, the aqueous solvent can also rehydrate and/or release sample components. In some embodiments, the sample can be mixed in the aqueous solvent. Regardless, the presence the aqueous solvent not only rehydrates the matrix of the matrix zones or reagent zones, it provides a medium for diffusive mixing and contact between the probes and other reagents previously sequestered in the matrix zones and sample and other reagents disposed on the substrate or on other substrates in liquid communication with said substrate.

As noted above, in practice of the invention, in some embodiments the sample can be mixed with the aqueous solvent so that it is present when disposed on the substrate. In some embodiments, other reagents can also be present in the aqueous solvent. Other reagents provided in the solvent can be selected to complement reagents sequestered in the matrix zones. In practice, most of all of the other reagents selected to be present in a hybridization reaction will be present in either or both of; 1 the matrix zone or reagent zone; or 2) the aqueous solvent so that they are present in the proper concentration/proportion to effect proper operation of the hybridization assay at each reagent zone or matrix zone. If not present in the matrix zone, reagent zone and/or the aqueous solvent, they can be added by one or more additional steps.

E. Other Reagents

The 'other reagents' used in practice of this invention generally comprise buffers, salts, detergents, fixatives and any other water soluble composition useful to perform a hybridization assay. As noted above, these can be divided whereby some are sequestered in the matrix, some are found in the aqueous solvent and optionally some added by other means. In some embodiments, it may be possible to sequester all 'other reagents' in the matrix film, reagent zones or matrix zones. In some embodiments, it may be possible to add all of the 'other reagents' by way of the aqueous solvent. In some embodiments it may be possible to add all of the 'other reagents' by way of the other means.

Some examples of the 'other reagents' that may be present in the assays practiced according to this invention include: formamide, a detergent such as Triton-X100 ®, a chelating agent such as ethylenediaminetetraacetic acid (EDTA), a buffer like N-(2-Hydroxyethyl)piperazine-N'-(4-butanesulfonic acid (HepBS), salts such as sodium chloride (NaCl) or a phosphate salt and polyethylene glycol.

F. Polymer Cap

The polymer cap is a layer of polymer that is deposited over some or all of the matrix film, matrix zones or reagent zones. The polymer cap is optional but is useful to avoid disruption/dislocation of the matrix (and the embedded reagents) when aqueous solvent (e.g. rehydration buffer or fluid) is first added to the matrix to rehydrate it.

The polymer cap is generally selected to be capable of rehydration with water or rehydration fluid (e.g. rehydration buffer) and also to be soluble in an organic solvent such as for example, ethanol, acetonitrile, methylene chloride, chloroform, benzene or dichloroethane. The polymer cap will generally be soluble in water or aqueous buffer as well as in at least one organic solvent that does not substantially dissolve the matrix (i.e. an organic solvent (or mixture of organic solvents) in which the matrix-forming prolonged-dissolution hydrophilic polymer is not substantially soluble). An example of a suitable polymer that can be used as a polymer cap is polyethylene oxide (PEO).

Generally the polymer cap can be applied to a matrix or a matrix film by depositing, such as by depositing, dispensing or spraying a solution comprising the polymer at the desired location and permitting solvent to evaporate. In some embodiments, the solution can be applied and spin coated to cover some or all of the matrix or matrix film.

G. Samples

In the practice of this invention, the sample is typically a fluid of biological origin or a liquid comprising a fluid of biological origin. Any microorganisms in the sample are assumed to be present in a concentration high enough so that there are cells of the target organism(s) in contact with or in the close proximity of each matrix zone or reagent zone, as applicable. Samples suitable for the practice of the invention include positive blood cultures, bronchoalveolar lavage, urine and other bodily fluids. Other examples are fluids collected from the environment and from foods or food processing. Samples derived from culture (growth) of low titer specimens are generally suitable for the practice of the invention as would be samples in which the microorganisms have been enriched or concentrated such as by centrifugation or filtration. The invention can also be useful for samples in which the cells of interest are mammalian cells. In samples of human or animal origin, such cells include blood cells, epithelial cells, endothelial cells, stem cells, fetal cells and cancer cells.

H. Suitable Hybridization Conditions

The extent and stringency of hybridization is controlled by a number of factors well known to those of ordinary skill in the art. These factors include the concentration of chemical denaturants such as formamide, ionic strength, detergent concentration, pH, the presence or absence of chaotropic agents, temperature, the concentrations of the probe(s) and quencher(s) and the time duration of the hybridization reaction. Suitable hybridization conditions can be experimentally determined by examining the effect of each of these factors on the extent and stringency of the hybridization reaction until conditions providing the required extent and stringency are found. The applicants have found that the matrix-forming prolonged-dissolution hydrophilic polymers of the invention exhibit the desired dissolution behavior under conditions suitable for hybridization reactions involving peptide nucleic acid probes and other probe types.

Dextran sulfate is a component of many hybridization buffers. Among other effects, it can increase the effective probe concentration by excluding it from the volume of the dextran polymer.

5. Various Embodiments of the Invention

It should be understood that the order of steps or order for performing certain actions is immaterial so long as the present teachings remain operable or unless otherwise specified. Moreover, in some embodiments, two or more steps or actions can be conducted simultaneously so long as the present teachings remain operable or unless otherwise specified.

This invention pertains to devices, compositions and methods that can be used for the rapid determination of microorganisms, cells and other analytes of interest (e.g. a nucleic acid target) as well as for determining associated properties of said microorganisms, cells and analytes. For example, said devices, compositions and/or methods can be applied to the determination of a trait of a microorganism present in a sample. Said devices, compositions and methods utilize prolonged-dissolution hydrophilic polymers to encapsulate hybridization probes and optionally other assay reagents within two or more reagent zones and/or matrix zones disposed on the surface of a substrate. Each reagent zone and/or matrix zone can be designed as a separate assay. Thus, a plurality of assays can be performed on a single substrate. In some embodiments, devices can be supplied in a form ready for a customer to rapidly perform one or a plurality of assays.

In some embodiments, a sample can be encapsulated in the prolonged-dissolution hydrophobic polymer and then rehydrated by contact with an aqueous liquid. In some embodiments, a sample can be dispersed in an aqueous liquid and said mixture of liquid comprising said sample then contacted with the reagent zones and/or matrix zones to perform an assay.

Regardless of the exact method, hybridization probes (and optionally sample) encapsulated in the reagent zones and/or matrix zones are released upon rehydration of the prolonged-dissolution hydrophobic polymer. Upon release, the hybridization probes can then interact with available sample and thereby provide an assay result. Generally there is no limitation on the hybridization assay type that can be performed using the compositions, devices and methods disclosed herein.

Compositions

In some embodiments, this invention pertains to a composition wherein said composition comprises at least one hybridization probe comprising a linked fluorescent label and at least one hybridization probe comprising a linked quencher moiety. Said hybridization probe comprising a linked fluorescent label can be configured to be capable of at least partially hybridizing to said hybridization probe comprising a linked quencher moiety as well as to a target sequence of interest, such as a target sequence within a microorganism of interest. In some embodiments, the linked fluorescent label and the linked quencher moiety are on the same hybridization probe; a configuration often termed a molecular beacon. Probes of these configurations are described in U.S. Pat. No. 6,355,421, incorporated herein by reference, inter alia, for their description of such probes and for a description of their associated methods of use.

In some embodiments, the hybridization probe comprising the linked fluorescent label and the hybridization probe comprising the linked quencher moiety are separate entities. The hybridization probe comprising the linked fluorescent label can be fully complementary to the hybridization probe comprising the linked quencher moiety, or the hybridization probe comprising the linked fluorescent label can be partially complementary to the hybridization probe comprising the linked quencher moiety. Probes of the latter configuration (a 'detection complex') that are suitable for performing target sequence analysis (including microorganism analysis) are described in U.S. Pat. No. 6,361,942, U.S. Pat. No. 6,607,889 and U.S. Pat. No. 6,649,349; all of which are incorporated herein by reference, inter alia, for their description of such probes and for the description of their associated methods of use.

It is to be understood, however, that it is not important whether or not the hybridization probe comprising a linked fluorescent label is actually hybridized to said hybridization probe comprising a linked quencher moiety (thereby forming said detection complex) when said hybridization probe comprising the linked fluorescent label interacts with a target sequence to form the probe/target complex. Rather, the presence of the hybridization probe comprising a linked quencher moiety in assays of this type is useful for suppressing the fluorescent signal of hybridization probes comprising the linked fluorescent label that remain unbound to a target sequence. In this way, the assay can be simplified as it can be performed without removal of excess fluorescently labeled probes and other reagents, for example, by use of a washing step. Examples of such assay and associated methods for performing assays requiring no washing steps can be found in U.S. Pat. No. 6,905,824 to Rigby et al., incorporated herein by reference for, inter alia, its description of 'no wash' assay formats.

According to the present invention, said composition may further comprise at least one matrix-forming prolonged-dissolution hydrophilic polymer. In some embodiments, said matrix-forming prolonged-dissolution hydrophilic polymer forms a matrix that shapes the bulk volume of said composition. Said matrix-forming prolonged-dissolution hydrophobic polymer embeds and/or encapsulates said hybridization probe or probes and optionally other reagents that may be present when the composition is formed or thereafter incorporated therein.

In some embodiments, said composition can be formed by permitting solvent of an aqueous solution comprising the: i) at least one hybridization probe comprising a linked fluorescent label; ii) at least one hybridization probe comprising a linked quencher moiety; and iii) at least one matrix-forming prolonged-dissolution hydrophilic polymer (and optionally other reagents) to evaporate. Evaporation of said solvent of said solution can produce a gel, semi-solid or solid.

Said gel, semi-solid or solid can form what is sometimes referred to herein as a matrix zone. Said 'matrix zones' can exist as independent compositions on a surface of a substrate wherein each matrix zone can comprise one or more hybridization probes and optionally other reagents used for an assay that can be performed at, or in close proximity to, said matrix zone. Said gel, semi-solid or solid 'matrix zone' is characterized in that it does not flow or substantially move under the influence of gravity. Without intending to be bound, it is believed that said hybridization probes and other reagents incorporated into said 'matrix zone' by said evaporative method are fairly homogeneously distributed throughout said matrix zone. Said belief is at least partially based on the observation that said matrix zones form with included fluorescent probes appear to be homogeneously fluorescent when observed under a microscope. Thus, in some embodiments, said composition is a matrix zone.

In some embodiments, said composition can be formed by permitting solvent of an aqueous solution comprising the at least one matrix-forming prolonged-dissolution hydrophilic polymer (optionally including probes and other reagents) to evaporate on a surface of a substrate to thereby form a matrix film. In some embodiments, the film is generated by spin coating a volume of the aqueous solution on the surface of a substrate. Evaporation of said solvent of said solution can produce a gel, semi-solid or solid matrix film on the surface of the substrate.

In some embodiments, the at least one hybridization probe comprising a linked fluorescent label and/or the at least one hybridization probe comprising a linked quencher moiety can be disposed at a unique area/location on said matrix film to thereby form a reagent zone. In some embodiments, the at least one hybridization probe comprising a linked fluorescent label and the at least one hybridization probe comprising a linked quencher moiety can, for example, be disposed at said unique area/location by dissolving them in an aqueous solution, applying said solution to the location/area of the matrix film and then allowing solvent of said aqueous solution to evaporate. Alternatively, said at least one hybridization probe comprising a linked fluorescent label and at least one hybridization probe comprising a linked quencher moiety could be disposed by applying a small section of a matrix film at said area/location wherein said at least one hybridization probe comprising a linked fluorescent label and at least one hybridization probe comprising a linked quencher moiety stand disposed.

A matrix film can comprise a plurality of reagent zones. Each of said 'reagent zones' can exist as independent areas/locations on a surface of a substrate that comprise one or more hybridization probes and optionally other reagents used for an assay that can be performed at, or in close proximity to said reagent zone. Thus, in some embodiments, said composition is a matrix film comprising one or more reagent zones. In some embodiments, the matrix film comprises two or more reagent zones. In some embodiments, said composition is a matrix film comprising 5 or more reagent zones.

In some embodiments, said at least one hybridization probe comprising a linked fluorescent label is a peptide nucleic acid probe. In some embodiments, said at least one hybridization probe comprising a linked quencher moiety is a peptide nucleic acid probe. In some embodiments, both of: i) said at least one hybridization probe comprising a linked fluorescent label and ii) at least one hybridization probe comprising a linked quencher moiety are peptide nucleic acid probes.

In some embodiments, this invention pertains to a composition comprising: i) at least one peptide nucleic acid probe; and ii) at least one matrix-forming prolonged-dissolution hydrophilic polymer, wherein said composition is a gel, semi-solid or solid. Said compositions can be formed as described above except that in some embodiments, said at least one hybridization probe comprising a linked fluorescent label and/or said at least one hybridization probe comprising a linked quencher moiety can be substituted for said at least one peptide nucleic acid probe. Accordingly, said compositions can exist as a matrix zone or a reagent zone as described above.

In some embodiments, compositions disclosed herein can be disposed on a substrate.

In some embodiments, compositions disclosed herein can further comprise a buffer.

In some embodiments, compositions disclosed herein can further comprise one or more distinct reagent zones.

While formation of the compositions may evaporation of an aqueous solvent, there is no requirement that all water and/or other solvent is completely removed. Rather, it is merely sufficient for the evaporation of solvent to produce a gel, semi-solid or solid characterized in it does not flow or substantially move under the influence of gravity. Thus, in some embodiments, the composition can further comprise residual water.

As noted above, other reagents can be encapsulated in the composition. Said 'other reagents' can optionally comprise some or all of the other reagents that are useful for the proper performance of an assay. For example, hybridization assays often include use of a detergent. Consequently, in some embodiments, the composition can further comprise a detergent.

There are numerous types of polymers that can be used to produce a composition (either as a matrix zone or a reagent zone) suitable for use in embodiments of this invention. Generally, the polymer is selected to be compatible with the hybridization probes and other reagents selected for use in a particular assay. The polymer can also be selected to have the property such that when a composition comprising the matrix-forming prolonged-dissolution hydrophilic polymer is contacted with an aqueous solvent, rehydration is relatively slow and occurs over a period of seconds to minutes. In this way the hybridization probes and other reagents embedded or encapsulated in said matrix are temporarily immobilized and/or restrained from free diffusion into the aqueous solvent (sometime referred to herein as a 'rehydration fluid'). Some non-limiting examples of matrix-forming prolonged-dissolution hydrophilic polymers include, but are not limited to: multi-subunit sugar copolymers, pullulan, methyl cellulose, carboxymethyl cellulose, carboxyethyl cellulose, carboxypropyl cellulose, hydroxyethyl cellulose, hydroxypropyl cellulose, hydroxypropyl methyl cellulose, polyvinylalcohol(s), polyvinylpyrrolidones(s), polyacrylamide(s), polyacrylic acid(s), polyethyleneimines(s), pectins or mixtures of any two or more of the foregoing.

Mixtures

In some embodiments, this invention pertains to mixtures. Said mixtures can comprise an aqueous solvent, one or more hybridization probes, other reagents and at least one matrix-forming prolonged-dissolution hydrophilic polymer. Said mixtures can be used to prepare the matrix film, matrix zones or reagent zones as previously described.

In brief, to form said a matrix zone, said mixture can be applied to a substrate and then the aqueous solvent is permitted to evaporate until the gel, semi-solid or solid matrix zone is formed. The use of elevated temperature can be helpful in promoting the evaporation of the aqueous solvent. In some embodiment, the mixture can be spin coated to form a matrix film.

In brief, to form a reagent zone, said mixture can be applied to a specific area or location of a matrix film and then the aqueous solvent is permitted to evaporate until the gel, semi-solid or solid matrix zone is formed or reformed. The use of elevated temperature can be helpful in promoting the evaporation of the aqueous solvent.

Thus, in some embodiments, this invention pertains to a mixture comprising an aqueous solvent, at least one hybridization probe comprising a linked fluorescent label, at least one hybridization probe comprising a linked quencher moiety and at least one matrix-forming prolonged-dissolution hydrophilic polymer. Said mixture can, by evaporation of said aqueous solvent, thereby be used to produce a, matrix film, matrix zone or reagent zone comprising at least one hybridization probe comprising a linked fluorescent label, at least one hybridization probe comprising a linked quencher moiety and at least one matrix-forming prolonged-dissolution hydrophilic polymer.

Thus, in some embodiments, this invention pertains to a mixture comprising: 1) an aqueous solvent; 2) at least one hybridization probe comprising a linked fluorescent label or at least one hybridization probe comprising a linked quencher moiety; and 3) at least one matrix-forming prolonged-dissolution hydrophilic polymer. Said mixture can, by evaporation of said aqueous solvent, thereby be used to produce a matrix film, matrix zone or reagent zone comprising: 1) an aqueous solvent; 2) at least one hybridization probe comprising a linked fluorescent label or at least one hybridization probe comprising a linked quencher moiety; and 3) at least one matrix-forming prolonged-dissolution hydrophilic polymer.

In some embodiments, this invention further pertains to a mixture comprising an aqueous solvent, at least one peptide nucleic acid probe and at least one matrix-forming prolonged-dissolution hydrophilic polymer. Said mixture can, by evaporation of said aqueous solvent, thereby be used to produce a matrix zone or reagent zone comprising at least one peptide nucleic acid probe and at least one matrix-forming prolonged-dissolution hydrophilic polymer.

One Part Assay Devices (or Component Parts of a Two Part Assay Device)

The compositions as previously described can be used to store and localize hybridization probes and other reagents that can later be used in assays as described herein. Indeed, this invention contemplates embodiments whereby a plurality of matrix zones or reagent zones are disposed on a surface of a substrate and whereby each matrix zone or reagent zone is capable of performing a unique assay for one or more unique target sequences, microorganisms, cells, analytes and/or traits of interest (i.e. conditions of interest).

The plurality of matrix zones can be prepared by applying a plurality of mixtures (prepared as described above) to a substrate and permitting solvent from each mixture to evaporate until each matrix zone is formed on said substrate. A plurality of reagent zones can be prepared as described above.

The assay to be examined at each matrix zone or reagent zone can be performed by simply contacting it with sample to be tested and an aqueous solvent which rehydrates the matrix-forming prolonged-dissolution hydrophilic polymer. In some embodiments, the sample to be tested can be premixed with an aqueous solvent (sometimes referred to as a rehydration fluid). In some embodiments, the sample to be tested is also encapsulated in matrix-forming prolonged-dissolution hydrophilic polymer and makes contact with each matrix zone or reagent zone when said matrix-forming prolonged-dissolution hydrophilic polymer is rehydrated in the presence of an aqueous solvent.

Each matrix zone or reagent zone is typically physically separated in space (in two dimensional space on a substrate's surface) from another matrix zone or reagent zone although that is not an absolute requirement. Two or more matrix zones or reagent zones can overlap (in two dimensional space on said substrate's surface) but they typically do not. Any substrate comprising two or more matrix zones or reagent zones, once prepared, is ready for determining a plurality of conditions of interest in a sample. Therefore, in some embodiments, this invention pertains to an assay device (that could itself be considered a component part or a larger device) that comprises a plurality of matrix zones and/or reagent zones disposed on a substrate, which assay device is capable of being used to perform a plurality of determinations (at least one determination per matrix zone or reagent zone) of conditions of interest in a sample.

Therefore, in some embodiments, this invention pertains to an assay device comprising: i) a substrate comprising a surface; ii) at least two matrix zones disposed on said surface of said substrate wherein at least one of said at least two matrix zones comprises: a) at least one hybridization probe comprising a linked fluorescent label; b) at least one hybridization probe comprising a linked quencher moiety; and c) at least one matrix-forming prolonged-dissolution hydrophilic polymer. Each matrix zone can be a gel, semi-solid or solid. As noted above, each such assay device is therefore preloaded to perform a plurality of determinations (at least one determination per matrix zone) of conditions of interest in a sample. In this preloaded configuration, all that need be added is typically no more than the sample and an aqueous solvent in order to rehydrate the matrix-forming prolonged-dissolution hydrophilic polymer and carry out the assay.

Because the assay device is generally designed to make a plurality of determinations on a single sample, in some embodiments, the hybridization probe comprising a linked fluorescent label is different as compared with the hybridization probes at a second matrix zone of said at least two matrix zones. Generally each matrix zone comprises at least one hybridization probe of unique sequence as said unique hybridization probe facilitates a unique determination. In some embodiments of the assay device, for one or more of said matrix zones, at least one hybridization probe is a peptide nucleic acid probe.

In some embodiments of the assay device, said at least one hybridization probe comprising a linked fluorescent label is a peptide nucleic acid probe. In some embodiments of the assay device, said at least one hybridization probe comprising a linked quencher moiety is a peptide nucleic acid probe. In some embodiments of the device component, both of: i) said at least one hybridization probe comprising a linked fluorescent label and ii) said at least one hybridization probe comprising a linked quencher moiety are peptide nucleic acid probes.

In some embodiments, this invention pertains to an assay device comprising: i) a substrate comprising a surface; ii) at least two matrix zones disposed on said surface of said substrate wherein at least one of said at least two matrix zones comprises: a) at least one peptide nucleic acid probe; and b) at least one matrix-forming prolonged-dissolution hydrophilic polymer, wherein each matrix zone is a gel, semi-solid or solid.

The assay devices can comprise any number of individual matrix zones. The number of matrix zones on a single device is only limited by the size of the surface of the device and the size of the matrix zone needed to perform an assay of interest. In some embodiments, the assay device can comprise from 2 to 10 matrix zones. In some embodiments, the assay device can comprise from 2 to 20 matrix zones. In some embodiments, the assay device can comprise from 2 to 50 matrix zones. In some embodiments, the assay device can comprise from 2 to 100 matrix zones. In some embodiments, the assay device can comprise greater than 100 matrix zones. In some embodiments, the assay device can comprise greater than 1,000 matrix zones. In some embodiments, the assay device can comprise greater than 10,000 matrix zones. In some embodiments, the assay device can comprise greater than 100,000 matrix zones.

In some embodiments, the assay device can further comprise a buffer. In some embodiments, the assay device can further comprise residual water. In some embodiments, the assay device can further comprise a detergent.

In some embodiments, the assay device further comprises a polymer cap disposed on the substrate and wherein one or more of the matrix zones is located between the polymer cap and the substrate (See for example: FIG. 4).

As previously noted, some, or all, of the surface of a substrate can be coated with a layer of matrix film and then individual reagent zones can be disposed at unique areas/locations of said matrix film. Thus, in some embodiments, this invention pertains to an assay device comprising: i) a substrate comprising a surface; ii) a film of matrix disposed on said surface of said substrate wherein said film of matrix comprises a matrix-forming prolonged-dissolution hydrophilic polymer and at least two reagent zones; and iii) one or more reagents disposed at each of said reagent zones, wherein said film of matrix is a gel, semi-solid or solid and at least one reagent zone comprises a) at least one hybridization probe comprising a linked fluorescent label and at least one hybridization probe comprising a linked quencher moiety; or b) at least one peptide nucleic acid probe.

In some embodiments, the assay device comprises at least one reagent zone comprising a peptide nucleic acid probe. In some embodiments, the assay device comprises at least one reagent zone comprising: a) at least one hybridization probe comprising a linked fluorescent label; and b) at least one hybridization probe comprising a linked quencher moiety. In some embodiments of the assay device, at least two reagents zones of at least two reagent zones each comprise at least one hybridization probe that is different as compared with the other.

In some embodiments, each reagent zone of the assay device comprises at least one hybridization probe comprising a linked fluorescent label and at least one hybridization probe comprising a linked quencher moiety. In some embodiments, each reagent zone of the assay device comprises at least one peptide nucleic acid probe.

In some embodiments, the assay device further comprises a polymer cap disposed on the substrate and wherein some or all of the matrix film is located between the polymer cap and the substrate (See for example: FIG. 4).

The assay devices disclosed herein can comprise any number of individual reagent zones. The number of reagent zones on a single device is only limited by the size of the surface of the device and the size of the reagent zones needed to perform an assay of interest. In some embodiments, the assay device can comprise from 2 to 10 reagent zones. In some embodiments, the assay device can comprise from 2 to 20 reagent zones. In some embodiments, the assay device can comprise from 2 to 50 reagent zones. In some embodiments, the assay device can comprise from 2 to 100 reagent zones. In some embodiments, the assay device can comprise greater than 100 reagent zones. In some embodiments, the assay device can comprise greater than 1,000 reagent zones. In some embodiments, the assay device can comprise greater than 10,000 reagent zones. In some embodiments, the assay device can comprise greater than 100,000 reagent zones.

In some embodiments, the assay device can further comprise a buffer. In some embodiments, the assay device can further comprise residual water. In some embodiments, the assay device can further comprise a detergent.

In various embodiments of the assay device, the matrix-forming prolonged-dissolution hydrophilic polymer can be selected from the group consisting of: multi-subunit sugar copolymers, pullulan, methyl cellulose, carboxymethyl cellulose, carboxyethyl cellulose, carboxypropyl cellulose, hydroxyethyl cellulose, hydroxypropyl cellulose hydroxypropyl methyl cellulose, polyvinylalcohol(s), polyvinylpyrrolidones(s), polyacrylamide(s), polyacrylic acid(s), polyethyleneimines(s), pectin(s) or mixtures of any two or more of the forgoing.

As noted above, the matrix zones are disposed on a surface of a substrate in the assay device components described above. The shape of said surface can be selected based on the nature of the equipment to be used to examine the assay to make the determinations. In some embodiments, these assays can be performed on a flat or substantially flat surface such as a microscope slide. Microscopic analysis of microorganisms has long been performed in the clinical laboratory and hospital setting. Thus, in some embodiments, said substrate is a microscope slide. In some embodiments, the substrate is transparent. Because in some embodiments the assays can be performed with fluorescent hybridization probes and fluorescence can be determined where incident light and optical detection occurs above the plane of the surface, the substrate need not always be transparent.

Two (or More) Part Assay Devices

The device components previously described can be combined with other components to form an assay device comprising two or more component parts. Assay devices that represent some embodiments of this invention possess two substrates. For example, an assay device of this invention can comprise a microscope slide as a first substrate and a cover slip as a second substrate wherein the plurality of assays to be performed at each matrix zone or reagent zone occurs between a surface of the microscope slide and a surface of the cover slip.

For example, in some embodiments, the sample can be immobilized on the surface of the cover slip and the matrix zones or reagent zones immobilized on the microscope slide. It is also possible to invert the configuration such that the sample is immobilized on the surface of the microscope slide and the matrix zones or reagent zone immobilized on the cover slip. Thus, the plurality of assays determined by the plurality of matrix zones can be performed simply by disposing an aqueous solution between the cover slip and the microscope slide, waiting a period of time sufficient for the matrix-forming prolonged-dissolution hydrophilic polymer to rehydrate and the assay components to interact and then determining the results of each of the plurality of assays.

Consequently, in some embodiments, this invention pertains to an assay device comprising at least two component parts, wherein, 1) a first of said at least two component parts comprises: i) a first substrate comprising a first surface; ii) at least two matrix zones disposed on said first surface of said first substrate wherein at least one of said matrix zones comprises: a) at least one hybridization probe comprising a linked fluorescent label; b) at least one hybridization probe comprising a linked quencher moiety; and c) at least one matrix-forming prolonged-dissolution hydrophilic polymer; and 2) a second of said at least two device component parts comprises: i) a second substrate comprising a second surface; and ii) a sample disposed on said second surface. Said second surface is capable of being spaced away from said first surface by a narrow gap.

In some embodiments, this invention also pertains to an assay device comprising at least two component parts, wherein, 1) a first of said at least two component parts comprises: i) a first substrate comprising a first surface; ii) at least two matrix zones disposed on said first surface of said first substrate wherein at least one of said matrix zones comprises: a) at least one peptide nucleic acid probe; and b) at least one matrix-forming prolonged-dissolution hydrophilic polymer; and 2) a second of said at least two device component parts comprises: i) a second substrate comprising a second surface; and ii) a sample disposed on said second surface. Said second surface is capable of being spaced away from said first surface by a narrow gap.

In some embodiments, this invention further pertains to an assay device comprising at least two component parts, wherein, 1) a first of said at least two component parts comprises: i) a first substrate comprising a first surface; ii) at least two matrix zones disposed on said first surface of said first substrate wherein at least one of said matrix zones comprises: a) at least one hybridization probe comprising a linked fluorescent label; b) at least one hybridization probe comprising a linked quencher moiety; and c) at least one matrix-forming prolonged-dissolution hydrophilic polymer; and 2) a second of said at least two component parts comprises a second substrate comprising a second surface. Said second surface is capable of being spaced away from said first surface by a narrow gap.

In some embodiments, this invention yet further pertains to an assay device comprising at least two component parts, wherein, 1) a first of said at least two component parts comprises: i) a first substrate comprising a first surface; ii) at least two matrix zones disposed on said first surface of said first substrate wherein at least one of said matrix zones comprises: a) at least one peptide nucleic acid probe; and b) at least one matrix-forming prolonged-dissolution hydrophilic polymer; and 2) a second of said at least two component parts comprises a second substrate comprising a second surface. Said second surface is capable of being spaced away from said first surface by a narrow gap.

In some embodiments of the aforementioned assay devices, said at least two matrix zones are in gel, semi-solid or solid form. In some embodiments of the aforementioned assay devices, said first surface of said first substrate comprises from 2 to 20 matrix zones.

In some embodiments of the previously described assay devices, the first substrate can further comprise a polymer cap disposed on the substrate and wherein one or more of the matrix zones is located between the polymer cap and said first substrate.

In some embodiments, this invention yet still further pertains to an assay device comprising at least two component parts, wherein, 1) a first of said at least two component parts comprises: i) a first substrate comprising a first surface; ii) a matrix film disposed on said first surface; iii) at least two reagent zones disposed within said matrix film, wherein, a) said matrix film is formed using at least one matrix-forming prolonged-dissolution hydrophilic polymer; and b) at least one reagent zone comprises at least one hybridization probe comprising a linked fluorescent label and at least one hybridization probe comprising a linked quencher moiety; and 2) a second of said at least two component parts comprises a second substrate comprising a second surface. Said second surface is capable of being spaced away from said first surface by a narrow gap. In some embodiments, the second surface of the second substrate can further comprise sample disposed thereon.

In some embodiments, this invention yet still further pertains to an assay device comprising at least two component parts, wherein, 1) a first of said at least two component parts comprises: i) a first substrate comprising a first surface; ii) a matrix film disposed on said first surface; iii) at least two reagent zones disposed within said matrix film, wherein, a) said matrix film is formed using at least one matrix-forming prolonged-dissolution hydrophilic polymer; and b) at least one reagent zone comprises at least one peptide nucleic acid probe; and 2) a second of said at least two component parts comprises a second substrate comprising a second surface. Said second surface is capable of being spaced away from said first surface by a narrow gap. In some embodiments, the second surface of the second substrate can further comprise sample disposed thereon.

In some embodiments of the aforementioned assay devices, said at least two reagent zones are in gel, semi-solid or solid form. In some embodiments of the aforementioned assay devices, said first surface of said first substrate comprises from 2 to 20 reagent zones.

In some embodiments of the previously described assay devices, the first substrate can further comprise a polymer cap disposed on the first surface of the first substrate and wherein some or all of the matrix film is located between the polymer cap and said first surface of the first substrate.

In some embodiments, the assay device is being used to perform an assay. Consequently, in some embodiments, a liquid can be disposed between the first surface of the first substrate and the second surface of the second substrate. Said liquid can be water or an aqueous solution. The aqueous solution can be referred to as a rehydration fluid or rehydration buffer. In some embodiments, said liquid can comprise sample to be tested.

In some embodiments, the assay device is readied for use, but is not yet being used. It is an advantage of this invention that in some embodiments, the assay device component parts and the assay devices appear to be stable for long periods of time and therefore can be prepared and then stored. Thus, in some embodiments, said assay device comprises at least two matrix zones or matrix films that are in gel, semi-solid or solid form.

In some embodiments, the matrix zone and/or reagent zones of the assay device comprise residual water. In some embodiments, the matrix zone and/or reagent zones of the assay device comprise a buffer and/or a detergent.

In some embodiments, the matrix-forming prolonged-dissolution hydrophilic polymer of the assay device is selected from the group consisting of: multi-subunit sugar copolymers, pullulan, methyl cellulose, carboxymethyl cellulose, carboxyethyl cellulose, carboxypropyl cellulose, hydroxyethyl cellulose, hydroxypropyl cellulose hydroxypropyl methyl cellulose, polyvinylalcohol(s), polyvinylpyrrolidones(s), polyacrylamide(s), polyacrylic acid(s), polyethyleneimines(s), pectin(s) or mixtures of any two or more of the forgoing.

In some embodiments, said first surface of said first substrate is flat or substantially flat. In some embodiments, said second surface of said second substrate is flat or substantially flat. An example of such an embodiment is a microscope slide and a cover slip. In such an embodiment, said first surface of the first substrate and said second surface of the second substrate can be separated by a narrow gap.

In some embodiments of the aforementioned assay devices, at least one of said first substrate and second substrate is transparent.

Examples of the aforementioned assay devices are illustrated in FIGS. 1-4. Said FIGS. 1-4 are illustrations of the invention using microscope slides and cover slips as examples. It is to be understood that these are provided for illustration purposes only and are not intended to be limiting in any way.

With reference to FIG. 1A, 30 denotes a microscope cover slip with dried sample 35 disposed on substantially all of one surface. In the illustration, 20 denotes a microscope slide as a substrate and 10 denotes one of a plurality (in this case 5 matrix zones are illustrated) of matrix zones disposed on a surface of said microscope slide. A drop of rehydration fluid is illustrated by 40.

Figure 1B:
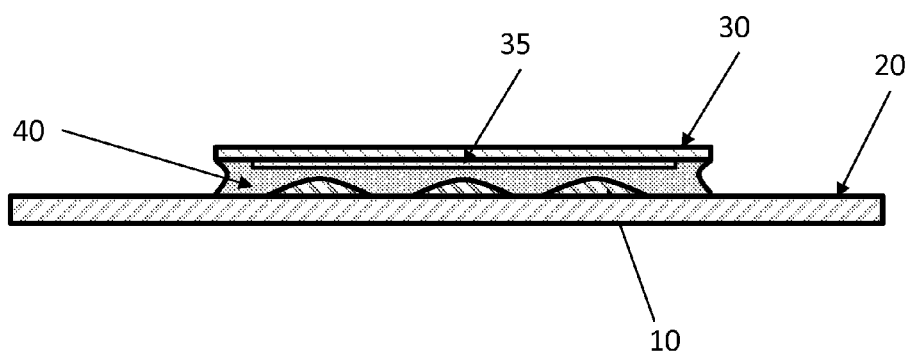

The elements illustrated in FIG. 1A can be assembled as illustrated in FIG. 1B to perform a plurality of assays. With reference to FIG. 1B, showing a cross-sectional view of the assembled elements, 20 denotes the microscope slide having a plurality of matrix zones 10 disposed on one surface. The coverslip 30, comprises the sample 35, disposed on one surface. As illustrated, the surface of the microscope slide 20 comprising the matrix zones and the surface of the coverslip 30 comprising the sample are arranged so that they are facing each other and substantially parallel with the rehydration fluid 40 disposed therebetween. This forms a narrow gap between the two surfaces. As the matrix-forming prolonged-dissolution hydrophilic polymer rehydrates, the sample, the hybridization probes and the other reagents are released such that they can interact so that the assay at each matrix zone can be performed. After a suitable amount of time has lapsed, the result of the hybridization assay can be determined.

Figure 2A:
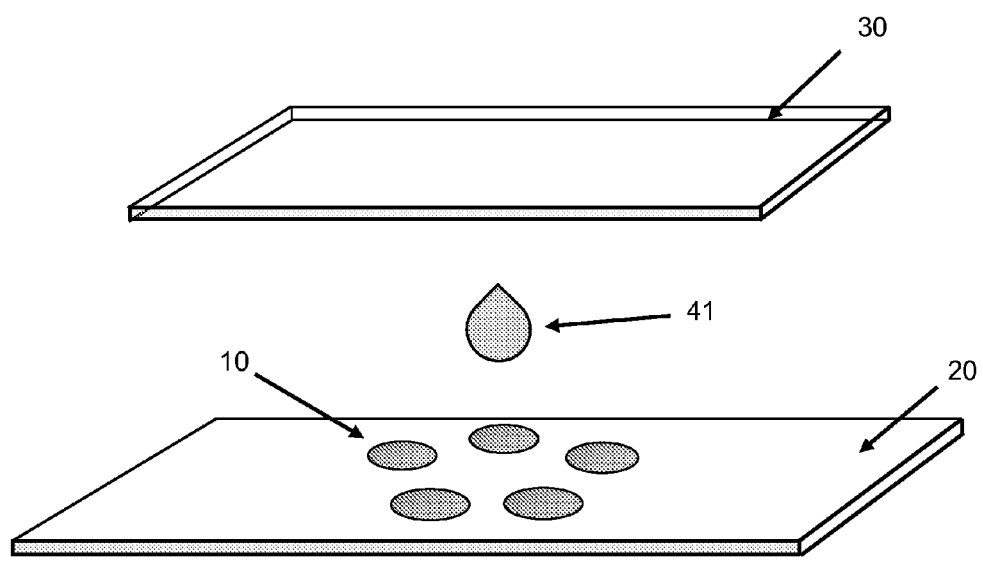
FIG. 2A illustrates the individual components of said assay and FIG. 2B illustrates the components as assembled to perform the assay.

As noted above, it is not necessary that the sample be disposed on the coverslip but can be added with the rehydration fluid or separately, for example in a separate fluid. With reference to FIG. 2A, 30 denotes a microscope cover slip. In the illustration, 20 denotes a microscope slide as a substrate and 10 denotes one of a plurality (in this case 5 matrix zones are illustrated) of matrix zones disposed on a surface of said microscope slide. A drop of rehydration fluid with sample mixed therein is illustrated by 41.

Figure 2B:
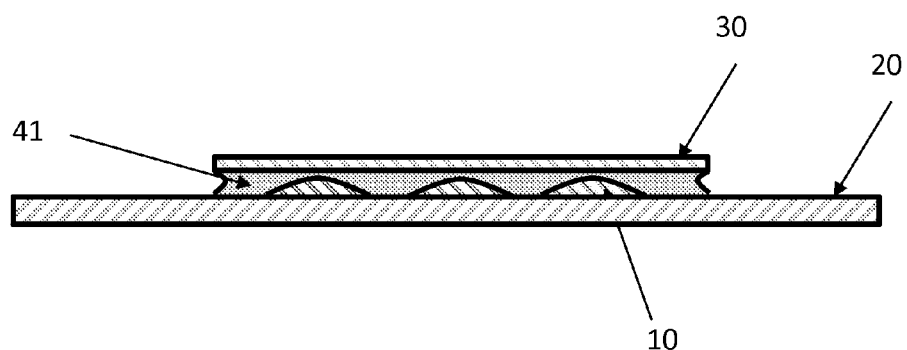

The elements illustrated in FIG. 2A can be assembled as illustrated in FIG. 2B to perform a plurality of assays. With reference to FIG. 2B, showing a cross-sectional view of the assembled elements, 20 denotes the microscope slide having a plurality of matrix zones 10 disposed on one surface. As illustrated, the surface of the microscope slide 20 comprising the matrix zones and one surface of the coverslip 30 are arranged so that they are facing each other and substantially parallel with the rehydration fluid comprising sample 41 disposed therebetween. This forms a narrow gap between the two surfaces. As the matrix-forming prolonged-dissolution hydrophilic polymer rehydrates, the sample, the hybridization probes and the other reagents are can interact so that the assay at each matrix zone can be performed. After a suitable amount of time has lapsed, the result of the hybridization assay can be determined.

As discussed above, the assays can be performed using reagent zones. An example of such an assay is illustrated in FIG. 3.

Figure 3A:
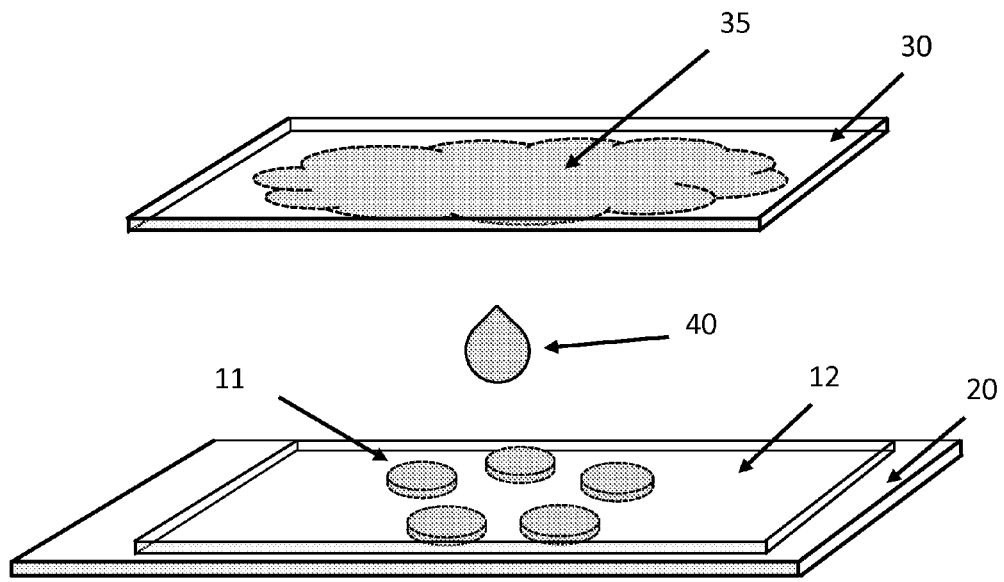
FIG. 3A illustrates the individual components of said assay and FIG. 3B illustrates the components as assembled to perform the assay.

With reference to FIG. 3A, 30 denotes a microscope cover slip with dried sample 35 disposed on substantially all of one surface. In the illustration, 20 denotes a microscope slide as a substrate. One surface of said microscope slide is coated with a matrix film 12. Disposed within said matrix film is a plurality (in this case 5 reagent zones are illustrated) of reagent zones. A drop of rehydration fluid is illustrated by 40.

Figure 3B:
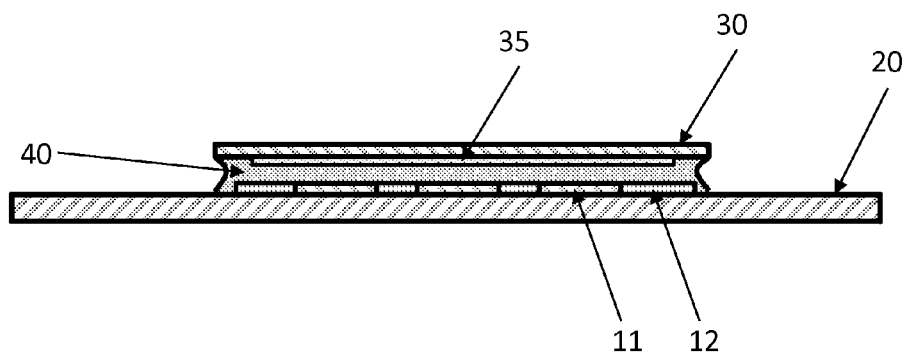

The elements illustrated in FIG. 3A can be assembled as illustrated in FIG. 3B to perform a plurality of assays. With reference to FIG. 3B, showing a cross-sectional view of the assembled elements, 20 denotes the microscope slide comprising the matrix film 12 and a plurality of reagent zones 11 disposed on one surface. The coverslip 30, comprises the sample 35, disposed on one surface. As illustrated, the surface of the microscope slide 20 comprising the matrix film and integrated reagent zones and the surface of the coverslip 30 comprising the sample are arranged so that they are facing each other and substantially parallel with the rehydration fluid 40 disposed therebetween. This forms a narrow gap between the two surfaces. As the matrix-forming prolonged-dissolution hydrophilic polymer rehydrates, the sample, the hybridization probes and the other reagents are released such that they can interact so that the assay at each reagent zone can be performed. After a suitable amount of time has lapsed, the result of the hybridization assay can be determined.

As discussed above, the assays can be performed with matrix zones having polymer caps. An example of such an assay is shown in FIG. 4.

Figure 4A:
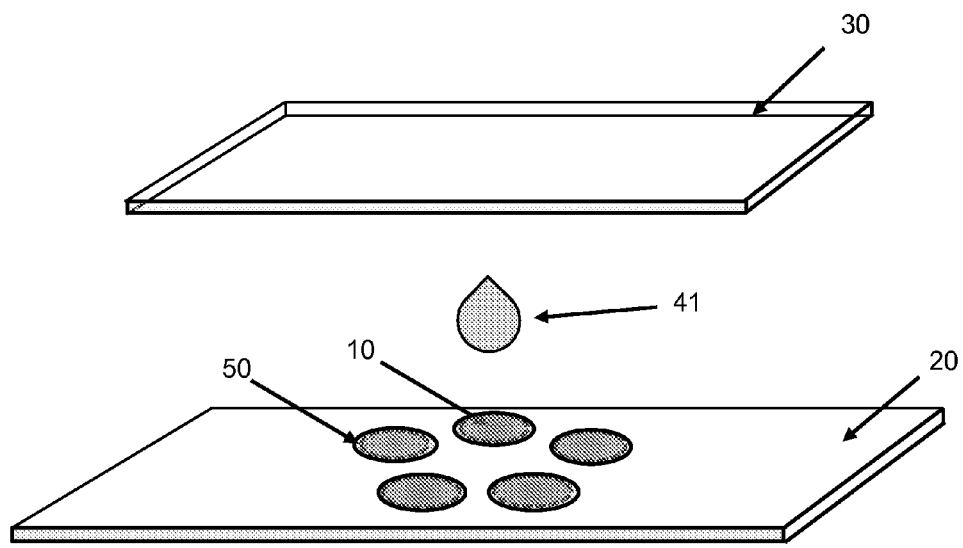
FIG. 4A illustrates the individual components of said assay and FIG. 4B illustrates the components as assembled to perform the assay.

With reference to FIG. 4A, 30 denotes a microscope cover slip. In the illustration, 20 denotes a microscope slide as a substrate and 10 denotes one of a plurality (in this case 5 matrix zones are illustrated) of matrix zones disposed on a surface of said microscope slide. 50 denotes one of the polymer caps disposed to cover the matrix zones 10. A drop of rehydration fluid with sample mixed therein is illustrated by 41.

Figure 4B:
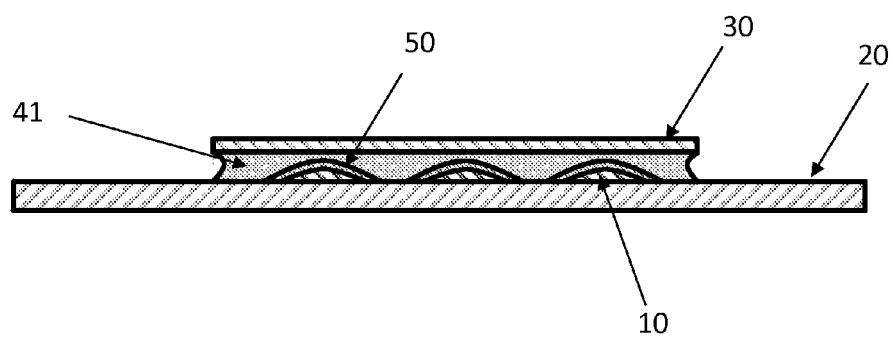

The elements illustrated in FIG. 4A can be assembled as illustrated in FIG. 4B. With reference to FIG. 4B, showing a cross-sectional view of the assembled elements, 20 denotes the microscope slide having a plurality of matrix zones 10 disposed on one surface. Each matrix zone 10, is covered by a polymer cap 50. As illustrated, the surface of the microscope slide 20 comprising the matrix zones and one surface of the coverslip 30 are arranged so that they are facing each other and substantially parallel with the rehydration fluid comprising sample 41 disposed therebetween. This forms a narrow gap between the two surfaces. As the matrix-forming prolonged-dissolution hydrophilic polymer and its polymer cap rehydrate, the sample, the hybridization probes and the other reagents are can interact so that the assay at each matrix zone can be performed. After a suitable amount of time has lapsed, the result of the hybridization assay can be determined.

It is to be understood that without showing all the details, an equivalent illustration that combines the features of FIG. 2 and FIG. 3 could be prepared to illustrated how a substrate comprising reagent zones could be used with a rehydration fluid comprising sample as compared with disposing said sample on the coverslip as shown in FIG. 1 and FIG. 3.

Methods

Assay methods associated with this invention can be practiced using the aforementioned assay devices as well as other aspects of the invention as disclosed herein. Practice of the assays can be used to determine microorganisms, cells, analytes (e.g. target nucleic acids), traits or other conditions of interest associated with a target sequence. The non-limiting Examples described below demonstrate the feasibility and simplicity of the inventive methods disclosed herein.

Thus, in some embodiments, this invention pertains to a method comprising: A) providing an assay device comprising at least two component parts, wherein, 1) a first of said at least two component parts comprises: i) a first substrate comprising a first surface; ii) at least two matrix zones disposed on said first surface of said first substrate wherein at least one of said at least two matrix zones comprises: a) at least one hybridization probe comprising a linked fluorescent label; b) at least one hybridization probe comprising a linked quencher moiety; and c) at least one matrix-forming prolonged-dissolution hydrophilic polymer; and 2) a second of said at least two device component parts comprises: i) a second substrate comprising a second surface; and ii) a sample disposed on said second surface; and B) disposing an aqueous liquid between said first surface of said first substrate and said second surface of said second substrate such that said first surface and said second surface are in liquid communication. An example of this embodiment is illustrated in FIG. 1B.

In some embodiments, said method can further comprise: C) waiting for a period of time sufficient for said matrix-forming prolonged-dissolution hydrophilic polymer to re-hydrate and for; a) said at least one hybridization probe comprising a linked fluorescent label; and b) said at least one hybridization probe comprising a linked quencher moiety present at said matrix zone to interact with each other and with said sample. The period of time needed will depend on the time it takes for the matrix-forming prolonged-dissolution hydrophilic polymer to re-hydrate and well as the time necessary for the probes to properly interact with each other and with sample components. Generally this will be from about 10 minutes to about 2 hours. However, it could be longer or shorter depending on the nature of the components and conditions of a particular assay.

In some embodiments, said method can further comprise: D) determining one or more conditions of interest of said sample based, at least in part, on how: a) said at least one hybridization probe comprising a linked fluorescent label; and b) said at least one hybridization probe comprising a linked quencher moiety interact with each other and with said sample at said matrix zone. With fluorescent probes, the determination can be made manually by observation under a fluorescent microscope. However, the determinations could be automated using computer analysis of images created with said microscope or by using slide scanners and the like.

In some embodiments of said method, at least two of said at least two matrix zones each comprise at least one hybridization probe comprising a linked fluorescent label and at least one hybridization probe comprising a linked quencher moiety and said method further comprises: D) determining one or more conditions of interest of said sample based, at least in part, on how each of said at least one hybridization probe comprising a linked fluorescent label and said at least one hybridization probe comprising a linked quencher moiety interact with each other and with said sample at each of said at least two of said at least two matrix zones.

Still further, in some embodiments of said method, each of said at least two matrix zones each comprise at least one hybridization probe comprising a linked fluorescent label and at least one hybridization probe comprising a linked quencher moiety and said method further comprises: D) determining one or more conditions of interest of said sample based, at least in part, on how each of said at least one hybridization probe comprising a linked fluorescent label and said at least one hybridization probe comprising a linked quencher moiety interact with each other and with said sample at each matrix zone.

In some embodiments, this invention pertains to a method comprising: A) providing an assay device comprising at least two component parts, wherein, 1) a first of said at least two component parts comprises: i) a first substrate comprising a first surface; ii) at least two matrix zones disposed on said first surface of said first substrate wherein at least one of said at least two matrix zones comprises: a) at least one peptide nucleic acid probe; and b) at least one matrix-forming prolonged-dissolution hydrophilic polymer; and 2) a second of said at least two device component parts comprises: i) a second substrate comprising a second surface; and ii) a sample disposed on said second surface; and B) disposing an aqueous liquid between said first surface of said first substrate and said second surface of said second substrate such that said first surface and said second surface are in liquid communication.

In some embodiments, said method can further comprise: C) waiting for a period of time sufficient for said matrix-forming prolonged-dissolution hydrophilic polymer to re-hydrate and for said at least one peptide nucleic acid probe to interact with said sample. The period of time needed will depend on the time it takes for the matrix-forming prolonged-dissolution hydrophilic polymer to re-hydrate and well as the time necessary for the probes to properly interact with each other and with sample components. Generally this will be from about 10 minutes to about 2 hours. However, it could be longer or shorter depending on the nature of the components and conditions of a particular assay.

In some embodiments, said method can further comprise: D) determining one or more conditions of interest of said sample based, at least in part, on how said at least one peptide nucleic acid probe interacts with said sample at said matrix zone. With fluorescent probes, the determination can be made manually by observation under a fluorescent microscope. However, the determinations could be automated using computer analysis of images created with said microscope or by using slide scanners and the like.

In some embodiments of said method, at least two of said at least two matrix zones each comprise a peptide nucleic acid probe and said method further comprises: D) determining one or more conditions of interest of said sample based, at least in part, on how each of said at least one peptide nucleic acid probe interacts with said sample at each of said at least two of said at least two matrix zones.

Still further, in some embodiments of said method, each of said at least two matrix zones each comprise a peptide nucleic acid probe and said method further comprises: D) determining one or more conditions of interest of said sample based, at least in part, on how each of said at least one peptide nucleic acid probe interacts with said sample at each matrix zone.

In some embodiments, this invention pertains to a method comprising: A) providing an assay device comprising at least two component parts, wherein, 1) a first of said at least two component parts comprises: i) a first substrate comprising a first surface; ii) at least two matrix zones disposed on said first surface of said first substrate wherein at least one of said matrix zones comprises: a) at least one hybridization probe comprising a linked fluorescent label; b) at least one hybridization probe comprising a linked quencher moiety; and c) at least one matrix-forming prolonged-dissolution hydrophilic polymer; and 2) a second of said at least two device component parts comprises a second substrate comprising a second surface; and B) disposing a sample and an aqueous liquid between said first surface of said first substrate and said second surface of said second substrate. Generally for this embodiment said first surface and said second surface are in liquid communication. An example of this embodiment of the method is illustrated in FIG. 2B.

In some embodiments, said method can further comprise: C) waiting for a period of time sufficient for said matrix-forming prolonged-dissolution hydrophilic polymer to re-hydrate and for: a) said at least one hybridization probe comprising a linked fluorescent label; and b) said at least one hybridization probe comprising a linked quencher moiety present at said matrix zone to interact with each other and with said sample. The period of time needed will depend on the time it takes for the matrix-forming prolonged-dissolution hydrophilic polymer to re-hydrate and well as the time necessary for the probes to properly interact with each other and with sample components. Generally this will be from about 10 minutes to about 2 hours. However, it could be longer or shorter depending on the nature of the components and conditions of a particular assay.

In some embodiments, said method can further comprise: D) determining one or more conditions of interest of said sample based on how: a) said at least one hybridization probe comprising a linked fluorescent label; and b) said at least one hybridization probe comprising a linked quencher moiety interact with each other and with said sample at each matrix zone. With fluorescent probes, the determination can be made manually by observation under a fluorescent microscope. However, the determinations could be automated using computer analysis of images created with said microscope or by using slide scanners and the like.

In some embodiments of said method, at least two of said at least two matrix zones each comprise at least one hybridization probe comprising a linked fluorescent label and at least one hybridization probe comprising a linked quencher moiety and said method further comprises: D) determining one or more conditions of interest of said sample based, at least in part, on how each of said at least one hybridization probe comprising a linked fluorescent label and said at least one hybridization probe comprising a linked quencher moiety interact with each other and with said sample at each of said at least two of said at least two matrix zones.

Still further, in some embodiments of said method, each of said at least two matrix zones each comprise at least one hybridization probe comprising a linked fluorescent label and at least one hybridization probe comprising a linked quencher moiety and said method further comprises: D) determining one or more conditions of interest of said sample based, at least in part, on how each of said at least one hybridization probe comprising a linked fluorescent label and said at least one hybridization probe comprising a linked quencher moiety interact with each other and with said sample at each matrix zone.

In some embodiments, this invention pertains to a method comprising: A) providing an assay device comprising at least two component parts, wherein, 1) a first of said at least two component parts comprises: i) a first substrate comprising a first surface; ii) at least two matrix zones disposed on said first surface of said first substrate wherein each of said at least two matrix zones comprises: a) at least one peptide nucleic acid probe; and b) at least one matrix-forming prolonged-dissolution hydrophilic polymer; and 2) a second of said at least two device component parts comprises a second substrate comprising a second surface; and B) disposing a sample and an aqueous liquid between said first surface of said first substrate and said second surface of said second substrate. Generally for this embodiment said first surface and said second surface are in liquid communication.

In some embodiments, said method can further comprise: C) waiting for a period of time sufficient for said matrix-forming prolonged-dissolution hydrophilic polymer to re-hydrate and for said at least one peptide nucleic acid probe to interact with said sample. The period of time needed will depend on the time it takes for the matrix-forming prolonged-dissolution hydrophilic polymer to re-hydrate and well as the time necessary for the probes to properly interact with each other and with sample components. Generally this will be from about 10 minutes to about 2 hours. However, it could be longer or shorter depending on the nature of the components and conditions of a particular assay.

In some embodiments, said method can further comprise: D) determining one or more conditions of interest of said sample based, at least in part, on how said at least one peptide nucleic acid probe interacts with said sample at said matrix zone. With fluorescent probes, the determination can be made manually by observation under a fluorescent microscope. However, the determinations could be automated using computer analysis of images created with said microscope or by using slide scanners and the like.

In some embodiments of said method, at least two of said at least two matrix zones each comprise a peptide nucleic acid probe and said method further comprises: D) determining one or more conditions of interest of said sample based, at least in part, on how each of said at least one peptide nucleic acid probe interacts with said sample at each of said at least two of said at least two matrix zones.

Still further, in some embodiments of said method, each of said at least two matrix zones each comprise a peptide nucleic acid probe and said method further comprises: D) determining one or more conditions of interest of said sample based, at least in part, on how each of said at least one peptide nucleic acid probe interacts with said sample at each matrix zone In some embodiments of the foregoing methods, one or more of said matrix zones further comprises a polymer cap disposed on the substrate and wherein said one or more matrix zones is located between the polymer cap and the substrate.

In some embodiments, this invention pertains to a method comprising: A) providing an assay device comprising at least two component parts, wherein, 1) a first of said at least two component parts comprises: i) a first substrate comprising a first surface; ii) a matrix film disposed on said surface; iii) at least two reagent zones disposed within said matrix film, wherein, a) said matrix film is formed using at least one matrix-forming prolonged-dissolution hydrophilic polymer; and b) at least one reagent zone comprises at least one hybridization probe comprising a linked fluorescent label and at least one hybridization probe comprising a linked quencher moiety; and 2) a second of said at least two device component parts comprises: i) a second substrate comprising a second surface; and ii) a sample disposed on said second surface; and B) disposing an aqueous liquid between said first surface of said first substrate and said second surface of said second substrate such that said first surface and said second surface are in liquid communication. An example of this embodiment is illustrated in FIG. 3B.

In some embodiments, said method can further comprise: C) waiting for a period of time sufficient for said matrix-forming prolonged-dissolution hydrophilic polymer to re-hydrate and for; a) said at least one hybridization probe comprising a linked fluorescent label; and b) said at least one hybridization probe comprising a linked quencher moiety present at said reagent zone to interact with each other and with said sample. The period of time needed will depend on the time it takes for the matrix-forming prolonged-dissolution hydrophilic polymer to re-hydrate and well as the time necessary for the probes to properly interact with each other and with sample components. Generally this will be from about 10 minutes to about 2 hours. However, it could be longer or shorter depending on the nature of the components and conditions of a particular assay.

In some embodiments, said method can further comprise: D) determining one or more conditions of interest of said sample based, at least in part, on how: a) said at least one hybridization probe comprising a linked fluorescent label; and b) said at least one hybridization probe comprising a linked quencher moiety interact with each other and with said sample at said reagent zone. With fluorescent probes, the determination can be made manually by observation under a fluorescent microscope. However, the determinations could be automated using computer analysis of images created with said microscope or by using slide scanners and the like.

In some embodiments of said method, at least two of said at least two reagent zones each comprise at least one hybridization probe comprising a linked fluorescent label and at least one hybridization probe comprising a linked quencher moiety and said method further comprises: D) determining one or more conditions of interest of said sample based, at least in part, on how each of said at least one hybridization probe comprising a linked fluorescent label and said at least one hybridization probe comprising a linked quencher moiety interact with each other and with said sample at each of said at least two of said at least two reagent zones.

Still further, in some embodiments of said method, each of said at least two reagent zones each comprise at least one hybridization probe comprising a linked fluorescent label and at least one hybridization probe comprising a linked quencher moiety and said method further comprises: D) determining one or more conditions of interest of said sample based, at least in part, on how each of said at least one hybridization probe comprising a linked fluorescent label and said at least one hybridization probe comprising a linked quencher moiety interact with each other and with said sample at each reagent zone.

In some embodiments, this invention pertains to a method comprising: A) providing an assay device comprising at least two component parts, wherein, 1) a first of said at least two component parts comprises: i) a first substrate comprising a first surface; ii) a matrix film disposed on said surface; iii) at least two reagent zones disposed within said matrix film, wherein, a) said matrix film is formed using at least one matrix-forming prolonged-dissolution hydrophilic polymer; and b) at least one reagent zone comprises at least one peptide nucleic acid probe; and 2) a second of said at least two device component parts comprises: i) a second substrate comprising a second surface; and ii) a sample disposed on said second surface; and B) disposing an aqueous liquid between said first surface of said first substrate and second surface of said second substrate such that said first surface and said second surface are in liquid communication.

In some embodiments, said method can further comprise: C) waiting for a period of time sufficient for said matrix-forming prolonged-dissolution hydrophilic polymer to re-hydrate and for said at least one peptide nucleic acid probe to interact with said sample. The period of time needed will depend on the time it takes for the matrix-forming prolonged-dissolution hydrophilic polymer to re-hydrate and well as the time necessary for the probes to properly interact with each other and with sample components. Generally this will be from about 10 minutes to about 2 hours. However, it could be longer or shorter depending on the nature of the components and conditions of a particular assay.

In some embodiments, said method can further comprise: D) determining one or more conditions of interest of said sample based, at least in part, on how said at least one peptide nucleic acid probe interacts with said sample at said reagent zone. With fluorescent probes, the determination can be made manually by observation under a fluorescent microscope. However, the determinations could be automated using computer analysis of images created with said microscope or by using slide scanners and the like.

In some embodiments of said method, at least two of said at least two reagent zones each comprise a peptide nucleic acid probe and said method further comprises: D) determining one or more conditions of interest of said sample based, at least in part, on how each of said at least one peptide nucleic acid probe interacts with said sample at each of said at least two of said at least two reagent zones.

Still further, in some embodiments of said method, each of said at least two reagent zones each comprise a peptide nucleic acid probe and said method further comprises: D) determining one or more conditions of interest of said sample based, at least in part, on how each of said at least one peptide nucleic acid probe interacts with said sample at each reagent zone.

In some embodiments, this invention pertains to a method comprising: A) providing an assay device comprising at least two component parts, wherein, 1) a first of said at least two component parts comprises: i) a first substrate comprising a first surface; ii) a matrix film disposed on said surface; iii) at least two reagent zones disposed within said matrix film, wherein, a) said matrix film is formed using at least one matrix-forming prolonged-dissolution hydrophilic polymer; and b) at least one reagent zone comprises at least one hybridization probe comprising a linked fluorescent label and at least one hybridization probe comprising a linked quencher moiety; and 2) a second of said at least two device component parts comprises a second substrate comprising a second surface; and B) disposing a sample and an aqueous liquid between said first surface of said first substrate and said second surface of said second substrate. Generally for this embodiment said first surface and said second surface are in liquid communication.

In some embodiments, said method can further comprise: C) waiting for a period of time sufficient for said matrix-forming prolonged-dissolution hydrophilic polymer to re-hydrate and for; a) said at least one hybridization probe comprising a linked fluorescent label; and b) said at least one hybridization probe comprising a linked quencher moiety present at said reagent zone to interact with each other and with said sample. The period of time needed will depend on the time it takes for the matrix-forming prolonged-dissolution hydrophilic polymer to re-hydrate and well as the time necessary for the probes to properly interact with each other and with sample components. Generally this will be from about 10 minutes to about 2 hours. However, it could be longer or shorter depending on the nature of the components and conditions of a particular assay.

In some embodiments, said method can further comprise: D) determining one or more conditions of interest of said sample based, at least in part, on how: a) said at least one hybridization probe comprising a linked fluorescent label; and b) said at least one hybridization probe comprising a linked quencher moiety interact with each other and with said sample at said reagent zone. With fluorescent probes, the determination can be made manually by observation under a fluorescent microscope. However, the determinations could be automated using computer analysis of images created with said microscope or by using slide scanners and the like.

In some embodiments of said method, at least two of said at least two reagent zones each comprise at least one hybridization probe comprising a linked fluorescent label and at least one hybridization probe comprising a linked quencher moiety and said method further comprises: D) determining one or more conditions of interest of said sample based, at least in part, on how each of said at least one hybridization probe comprising a linked fluorescent label and said at least one hybridization probe comprising a linked quencher moiety interact with each other and with said sample at each of said at least two of said at least two reagent zones.

Still further, in some embodiments of said method, each of said at least two reagent zones each comprise at least one hybridization probe comprising a linked fluorescent label and at least one hybridization probe comprising a linked quencher moiety and said method further comprises: D) determining one or more conditions of interest of said sample based, at least in part, on how each of said at least one hybridization probe comprising a linked fluorescent label and said at least one hybridization probe comprising a linked quencher moiety interact with each other and with said sample at each reagent zone.

In some embodiments, this invention pertains to a method comprising: A) providing an assay device comprising at least two component parts, wherein, 1) a first of said at least two component parts comprises: i) a first substrate comprising a first surface; ii) a matrix film disposed on said surface; iii) at least two reagent zones disposed within said matrix film, wherein, a) said matrix film is formed using at least one matrix-forming prolonged-dissolution hydrophilic polymer; and b) at least one reagent zone comprises at least one peptide nucleic acid probe; and 2) a second of said at least two device component parts comprises a second substrate comprising a second surface; and B) disposing a sample and an aqueous liquid between said first surface of said first substrate and said second surface of said second substrate. Generally for this embodiment said first surface and said second surface are in liquid communication.

In some embodiments, said method can further comprise: C) waiting for a period of time sufficient for said matrix-forming prolonged-dissolution hydrophilic polymer to re-hydrate and for said at least one peptide nucleic acid probe to interact with said sample at said reagent zone. The period of time needed will depend on the time it takes for the matrix-forming prolonged-dissolution hydrophilic polymer to re-hydrate and well as the time necessary for the probes to properly interact with each other and with sample components. Generally this will be from about 10 minutes to about 2 hours. However, it could be longer or shorter depending on the nature of the components and conditions of a particular assay.

In some embodiments, said method can further comprise: D) determining one or more conditions of interest of said sample based, at least in part, on how said at least one peptide nucleic acid probe interacts with said sample at said reagent zone. With fluorescent probes, the determination can be made manually by observation under a fluorescent microscope. However, the determinations could be automated using computer analysis of images created with said microscope or by using slide scanners and the like.

In some embodiments of said method, at least two of said at least two reagent zones each comprise a peptide nucleic acid probe and said method further comprises: D) determining one or more conditions of interest of said sample based, at least in part, on how each of said at least one peptide nucleic acid probe interacts with said sample at each of said at least two of said at least two reagent zones.

Still further, in some embodiments of said method, each of said at least two reagent zones each comprise a peptide nucleic acid probe and said method further comprises: D) determining one or more conditions of interest of said sample based, at least in part, on how each of said at least one peptide nucleic acid probe interacts with said sample at each reagent zone.

In some embodiments of the foregoing methods, one or more of said reagent zones further comprises a polymer cap disposed on the substrate and wherein said one or more reagent zones is located between the polymer cap and the substrate.

In some embodiments of the foregoing methods, the first substrate can further comprise a polymer cap disposed on the first surface of the first substrate and wherein some or all of the matrix film is located between the polymer cap and said first surface of the first substrate.

It is to be understood that the sample to be analyzed at each matrix zone and/or reagent zone by practice of certain of the aforementioned methods will be examined for the presence of a target sequence associated with the condition of interest. For example, in some embodiments an assay for a microorganism at a particular matrix zone or reagent zone, said at least one hybridization probe comprising a linked fluorescent label can be designed to possess a nucleobase sequence that is complementary to a unique target sequence in the said microorganism. In the assay, the hybridization probes comprising the linked fluorescent label can cross into the microorganism and hybridize to the target sequence thereby concentrating fluorescent signal within the microorganism. In examples where probes comprising a quencher moiety interact with hybridization probes comprising a fluorescent label, excess of the hybridization probes comprising the linked fluorescent label can bind to the hybridization probe comprising a linked quencher moiety, thereby quenching said fluorescent label and reducing background fluorescence in the assay. Thus, upon viewing the microscope slide (the first substrate) under fluorescent microscopy conditions, the microorganisms of the sample that are of interest based on selection of the hybridization probe comprising the linked fluorescent label present at a particular matrix zone or reagent zone can be determined.

It is to be understood that the sample to be analyzed at each matrix zone and/or reagent zone by practice of certain of the aforementioned method will be examined for the presence of a target sequence associated with the condition of interest. For example, in an assay for a microorganism at a particular matrix zone, said at least one peptide nucleic acid probe can be designed to possess a label and a nucleobase sequence that is complementary to a unique target sequence in the said microorganism. In the assay, the peptide nucleic acid hybridization probe can cross into the microorganism and hybridize to the target sequence thereby concentrating the label within the microorganism. Excess of the hybridization probes comprising the label can, for example, be washed away using conventional methods known in the art. Thus, upon examining the first substrate (e.g. a microscope slide) under suitable conditions necessary to determine the label, the microorganisms of the sample that are of interest based on selection of the peptide nucleic acid probe present at a particular matrix zone or reagent zone can be determined. In some embodiments, a no wash assay is performed.

As illustrated in the figures, if one is using a microscope slide as the first substrate to practice any of the aforementioned methods, the second substrate can be a microscope cover slip. In some embodiments, said sample can be directly dried down on said second substrate. In some embodiments, said sample can be mixed with an aqueous solvent and that solvent contacted with the first surface of the first substrate. In some embodiments, the sample can be mixed with the rehydration fluid (also sometimes referred to as the rehydration buffer).

When practicing the disclosed methods, at least the first surface of the first substrate is contacted with an aqueous fluid that is used to rehydrate the matrix-forming prolonged-dissolution hydrophilic polymer. Regardless, when the aqueous liquid is disposed between said first surface of said first substrate and said second surface of said second substrate such that said first surface and said second surface are in liquid communication, the components of the sample are able to interact with the hybridization probes and other reagents in each of the matrix zones and/or reagent zones.

In some respects, the practice of this invention is advantageous because; 1) the matrix-forming prolonged-dissolution hydrophilic polymer prevents reagent within the matrix zones and/or reagent zones from dissolving on contact with the aqueous solvent and thereby prevents that reagent from being carried by the initial convective flow of the aqueous solvent; and 2) once the matrix-forming prolonged-dissolution hydrophilic polymer is rehydrated, the reaction components are free to react across the defined matrix zones by diffusion. In the methods of the invention, Applicants have observed that multiple assays can be performed each at a different matrix zone and/or reagent zone on a single substrate with little or no crosstalk between reagents at each matrix zone as evidenced by the clarity and precision of the results.

Even more surprising has been the observation that the sample need not be immobilized to the second substrate. Rather, it can be disposed directly in solution onto the first substrate as previously described. Performing the assay in this way appears to be capable of producing similar clarity and precision of results.

For any of the aforementioned methods, in some embodiments, at least one of said first substrate and second substrate can be transparent. In some embodiments both the first substrate and the second substrate are transparent. In some embodiments, neither the first substrate nor the second substrate is transparent.

For any of the aforementioned methods, in some embodiments, said first surface of said first substrate can be flat or substantially flat. For any of the aforementioned methods, in some embodiments, said second surface of said second substrate can be flat or substantially flat. For any of the aforementioned methods, in some embodiments, both said first surface of said first substrate can be flat or substantially flat and said second surface of said second substrate can be flat or substantially flat. In some embodiments, the first surface of the first substrate and the second surface of the second substrate are separated by a narrow gap.

For certain of the aforementioned methods, in some embodiments, said first surface of said first substrate can comprise from 2 to 20 matrix zones. For certain of the aforementioned methods, in some embodiments, said first surface of said first substrate can comprise from 2 to 20 reagents zones.

For certain of the aforementioned methods, in some embodiments, one or more of said matrix zones may further comprise a buffer. For certain of the aforementioned methods, in some embodiments, one or more of said matrix zones may further comprise a detergent. For certain of the aforementioned methods, in some embodiments, one or more of said matrix zones may further comprise a fixing agent.

For certain of the aforementioned methods, in some embodiments, one or more of said reagent zones may further comprise a buffer. For certain of the aforementioned methods, in some embodiments, one or more of said reagent zones may further comprise a detergent. For certain of the aforementioned methods, in some embodiments, one or more of said reagent zones may further comprise a fixing agent.

For any of the aforementioned methods, said matrix-forming prolonged-dissolution hydrophilic polymer can be selected from the group consisting of: multi-subunit sugar copolymers, pullulan, methyl cellulose, carboxymethyl cellulose, carboxyethyl cellulose, carboxypropyl cellulose, hydroxyethyl cellulose, hydroxypropyl cellulose hydroxypropyl methyl cellulose, polyvinylalcohol(s), polyvinylpyrrolidones(s), polyacrylamide(s), polyacrylic acid(s), polyethyleneimines(s), pectin(s) or mixtures of any two or more of the forgoing.

Kits

In some embodiments, this invention is further directed to kits. In some embodiments, said kit comprises at least one composition as disclosed above under the heading: "Compositions". In some embodiments, said kit comprises at least one mixture as disclosed above under the heading: "Mixtures". In some embodiments, said kit comprises at least one mixture as disclosed above under the heading: "One Part Assay Devices" or under the heading "Two (or more) Part Assay Devices".

6. Advantages of Practicing this Invention

The above described invention permits numerous assays to be rapidly performed on a single sample. In embodiments of this invention, these analyses are performed on a single substrate, such as a microscope slide. This minimizes time to result and reduces labor costs associated with running multiple analyses of a single sample. When the numerous assays are combined on a single substrate, a significant reduction in reagents (both reagents used to create the assay device and reagents needed for a customer to perform the assay) can be achieved as compared with performing the various assays on multiple substrates. This can provide a significant reduction in production costs to the manufacturer and raw materials costs to the customer. With multiple assays in a single device, the need for preliminary testing to determine which of multiple assays is the correct one to be performed is eliminated. The laboratory simply runs all the assays at once. This allows results to be obtained more rapidly.

The resulting substrate-based embodiments of this invention exhibit additional surprising and advantageous properties. For example, it is known that PNA polymers have a strong affinity to glass surfaces (See: Peter E. Nielsen, Methods in Molecular Biology, vol. 208: Peptide Nucleic Acids, Methods and Protocols, Humana Press, Inc., page 267. It is also known that PNA polymers have a tendency to aggregate when stored in solution for extended periods of time (see: Tackett A J, Corey D R, Raney K D. (2002) Non-Watson-Crick interactions between PNA and DNA inhibit the ATPase activity of bacteriophage T4 Dda helicase. Nucleic Acids Res. 30, 950-957 and Braasch D. A. and Corey, D. R. (2001) Synthesis, analysis, purification and intracellular delivery of peptide nucleic acids. Methods, 23, 97-107.). It is further known that PNA polymers can be difficult to reconstitute (i.e. re-dissolve) when dried down on a surface or lyophilized. Applicants have surprisingly found that in embodiments of this invention, where PNA probes are applied in solution to glass slides (i.e. a glass microscope slide substrate) in combination with a matrix-forming prolonged-dissolution hydrophilic polymer and then the solvent is permitted to evaporate (i.e. an example of an 'assay device' as described herein), the PNA probes do not appear to substantially bind to the glass surfaces, do not appear form insoluble aggregates or exhibit problems re-dissolving as would be expected based on prior reports. Evidence for this conclusion is the lack of PNA residue where the matrix was spotted, the lack of observed aggregates in the reaction zone and the rapid hybridization results obtained in the assays described in the Examples below. It is also noteworthy and surprising that said 'assay devices' appear to be stable and can be stored for extended periods of time without significant reduction in performance (up to 12 weeks at 37° C.).

7. Examples

Aspects of the present teachings can be further understood in light of the following examples, which should not be construed as limiting the scope of the present teachings in any way.

Example 1 Heat-Fixed Sample

In this preparation the sample, blood culture is heat-fixed to the coverslip.
Probe and Quencher Polymer Solution Five different PNA assay mixtures were individually mixed 1:1 with a polymer solution. Four of the five PNA assay mixtures were based substantially on the *Staphylococcus, Enterococcus*, GNR Traffic Light and Yeast Traffic Light products available from AdvanDx, Inc. The Gram PNA assay mixture was substantially the same in composition to the commercial products except that the PNA probes were selected to detect gram positive bacteria, gram negative bacteria and yeast. They consist of fluorescein- and carboxytetramethylrhodamine-labeled, PNA probes (some incorporating e-linker solubility enhancing monomers) and shorter, complementary, 4-(dimethylaminoazo)benzene-4-carboxylic acid-labeled quenchers. The probes and quenchers for each assay mixture were diluted separately in a buffer containing 82.2 mM N-(2-Hydroxyethyl)piperazine-N'-(4-butanesulfonic acid) (HEPBS) (Sigma H6903), 0.1% sodium pyrophosphate decahydrate (Sigma 221368), 10 mM sodium chloride (Promega V4221), 5 mM ethylenediaminetetraacetic acid disodium salt (EDTA) (Promega V4231), 0.25% poly(ethylene glycol) (PEG) (Fluka 94646), 15% formamide (Sigma F9037) and remain separate until preparation of the probe and quencher polymer solution. The *Enterococcus* and Gram PNA assay mixtures were diluted 1:10 before mixing with the Polymer Solution. The Polymer Solution was prepared by adding 1 g of Poly(vinyl alcohol) (PVA) (Sigma P/N 363138) to 5 mL of nuclease free water and heating in a 95° C. water bath for one hour to dissolve completely.
Slides To prepare each microscope slide, 0.5 µL of probe and quencher containing polymer solution from each of the five assay mixtures (as received or diluted as described above) was pipetted onto a 25 mm×75 mm×1 mm glass microscope slide (Gold Seal 3010). The solution was spread into a 3.5 mm diameter circle. The five circles were arranged in an equidistant, circular pattern within a 19 mm circle. The circles were spaced 4.44 mm apart. The slide was then cured for an hour in a 70° C. oven.
Heat-Fixed Sample To prepare the coverslip comprising sample, 10 µL of blood culture was pipetted onto a 24 mm×50 mm glass coverslip (AdvanDx AC027) on a 55° C. heat block. One drop of QuickFix-1 (AdvanDx QFFIXBC1) was immediately mixed into the blood culture and spread into a 22 mm circle. The mixture was allowed to dry completely. 100 µL of QuickFix-2 (AdvanDx QFFIXBC1) was pipetted evenly over the entire circle and allowed to dry completely.
Rehydration The glass slide with the five spots (each spot representing a different PNA assay mixture) was placed on a 55° C. heat block. 40 µL of Rehydration Buffer (defined below) was pipetted onto the heat-fixed sample on the glass coverslip. Rehydration Buffer was made by adding 0.15 mL of formamide and 50 µL of 10% Triton X-100 (Sigma T8787) to 0.8 mL of nuclease free water. The coverslip was flipped over onto the glass slide so that all 5 assay mixtures are located beneath and within the heat-fixed sample area. The coverslip fit evenly onto the slide without hanging off any of the edges. The coverslip was not moved once it was in place.
Hybridization and Visualization Hybridization of the probes and target, if present, began after rehydration while the slide and coverslip remained on the 55° C. heat block for 15 minutes. Once the slide was removed from the heat block, the quenchers hybridized to any unbound probe. The slide was viewed on a fluorescence microscope equipped with a dual band pass filter (AdvanDx AC007) using a 20× objective to evaluate localization of the 5 PNA assay mixtures to within a 5.5 mm diameter circle. It was then evaluated using a 60× oil objective to interpret the results of the tests.
Results/Interpretation The Gram PNA assay was examined first. The results from this assay were used to determine which assay(s) should be examined next.
Gram PNA:
    Green Fluorescence—Gram positive bacteria
        If cocci in clusters, examine *Staphylococcus* assay.
        If cocci in pairs and chains, examine *Enterococcus* assay.
    Red Fluorescence—Gram negative bacteria
        If rods, examine Gram Negative assay.
    Yellow Fluorescence—Yeast
        If yeast morphology, examine Yeast assay.
    No Fluorescence—false positive blood culture
*Staphylococcus*:
    Green Fluorescence—*Staphylococcus aureus*
        Red Fluorescence—*Staphylococcus epidermidis, capitis, caprae, cohnii, haemolyticus*, or *pettenkoferi*
    No Fluorescence—negative
*Enterococcus*:
    Green Fluorescence—*Enterococcus faecalis*
        Red Fluorescence—Other *Enterococcus* sp. including *faecium*
    No Fluorescence—negative
Gram Negative:
    Green Fluorescence—*Escherichia coli*
        Red Fluorescence—*Pseudomonas aeruginosa*
        Yellow Fluorescence—*Klebsiella pneumoniae*
    No Fluorescence—negative
Yeast:
    Green Fluorescence—*Candida albicans*
        Red Fluorescence—*Candida glabrata*
        Yellow Fluorescence—*Candida parapsilosis*
    No Fluorescence—negative Example 2 In-Solution Sample In this preparation the sample, blood culture was heat treated, mixed with a buffered solution and remains in solution.

Probe and Quencher Polymer Solution

Five different PNA assay mixtures were individually mixed 1:1 with Polymer Solution. The five assay mixtures were those identified in Example 1. The probes and quenchers for these assay mixtures remain separate until preparation of the probe and quencher are added to the Polymer Solution. The *Enterococcus* and Gram PNA assay mixtures were diluted 1:10 before mixing with the Polymer Solution. The Polymer Solution was prepared by adding 1 g of PVA to 5 mL of nuclease free water and heating in a 95° C. water bath for one hour to dissolve completely.

Slides

To prepare the microscope slide, 0.5 µL of probe and quencher containing polymer solution from each of the five assay mixtures was pipetted onto a 25 mm×75 mm×1 mm glass microscope slide. The solution was spread into a 3.5 mm diameter circle. The five circles were arranged in an equidistant, circular pattern within a 19 mm circle. The circles were spaced 4.44 mm apart. The slide was then cured for an hour in a 70° C. oven.

In-Solution Sample

To prepare the sample, 0.2 mL of blood culture was heated in a 2 mL, round-bottom, microcentrifuge tube for 2 minutes in a dry 80° C. heat block. One part of cooled, heat-treated blood culture was mixed with 3 parts of All-In-One Buffer A (AIOBA) to produce Blood Culture Mixture. All-In-One Buffer A was 13 mM sodium chloride, 4.2 mM EDTA, 0.3% PEG, 18.9% formamide, 1% Triton X-100, 37.5 mM magnesium chloride (Boston Bioproducts MT-200), 120 mM Tris, pH 9 (JT Baker 4109-01), and 6 mM copper (II) sulfate anhydrous (Sigma C1297).

Rehydration

The glass slide with the five spots (each spot representing a PNA assay) was placed on a 55° C. heat block. 40 µL of the Blood Culture Mixture was pipetted onto a 24 mm×50 mm glass coverslip. The coverslip was flipped over onto the glass slide. The coverslip fit evenly onto the slide without hanging off any of the edges. The coverslip was not moved once it was in place.

Hybridization and Visualization

Hybridization of the probes and target, if present, began after rehydration while the slide and coverslip remained on the 55° C. heat block for 15 minutes. Once the slide was removed from the heat block, the quenchers hybridized to any unbound probe. The slide was viewed on a fluorescence microscope equipped with a dual band pass filter using a 20× objective to evaluate localization of the 5 PNA assays to within a 5.5 mm diameter circle. It was then evaluated using a 60× oil objective to interpret the results of the tests.

Results/Interpretation

The Gram PNA assay was examined first. The results from this assay were used to determine which assay(s) should be examined next.

Gram PNA:
  Green Fluorescence—Gram positive bacteria
    If cocci in clusters, examine *Staphylococcus* assay.
    If cocci in pairs and chains, examine *Enterococcus* assay.
  Red Fluorescence—Gram negative bacteria
    If rods, examine Gram Negative assay.
  Yellow Fluorescence—Yeast
    If yeast morphology, examine Yeast assay.
  No Fluorescence—False positive blood culture
*Staphylococcus:*
  Green Fluorescence—*Staphylococcus aureus*
    Red Fluorescence—*Staphylococcus epidermidis*, *capitis*, *caprae*, *cohnii*, *haemolyticus*, pettenkoferi
  No Fluorescence—negative

*Enterococcus:*
  Green Fluorescence—*Enterococcus faecalis*
    Red Fluorescence—Other *Enterococcus* sp. including *faecium*
  No Fluorescence—negative
Gram Negative:
  Green Fluorescence—*Escherichia coli*
    Red Fluorescence—*Pseudomonas aeruginosa*
    Yellow Fluorescence—*Klebsiella pneumoniae*
  No Fluorescence—negative
Yeast:
  Green Fluorescence—*Candida albicans*
    Red Fluorescence—*Candida glabrata*
    Yellow Fluorescence—*Candida parapsilosis*
  No Fluorescence—negative Example 3 Polymers as the Matrix-Forming Prolonged-Dissolution Hydrophilic Polymer Several classes of polymers were screened for functionality. They were judged on their ability to localize the probes quenchers, produce bright fluorescent signals and dark backgrounds. This example was performed primarily to ascertain the properties and identities of some exemplary polymers that could be used for practice of this invention.

Probe and Quencher Polymer Solution

The PNA *Enterococcus* assay mixture was mixed 1:1 with several polymer solutions. The probes and quenchers for the assay mixture remain separate until preparation of the probe and quencher polymer solutions. The *Enterococcus* assay mixture was diluted 1:10 before mixing with the polymers. The polymer solutions were prepared as indicated in Table 1.

Slides

Five 0.5 µL drops of probe and quencher containing polymer solution were pipetted onto a 25 mm×75 mm×1 mm glass microscope slide. The solution was spread into 3.5 mm diameter circles. The five circles were arranged in an equidistant, circular pattern within a 19 mm circle. The circles were spaced 4.44 mm apart. The slide was cured for an hour in a 70° C. oven.

Heat-Fixed Sample

10 µL of blood culture containing *Enterococcus faecalis* (Efs) and *faecium* (Efm) were pipetted onto a 24 mm×50 mm glass coverslip on a 55° C. heat block. One drop of QuickFix-1 was immediately mixed into the blood culture and spread into a 22 mm circle. The mixture was allowed to dry completely. 100 µL of QuickFix-2 were pipetted evenly over the entire circle and allowed to dry completely.

Rehydration

The glass slide with the *Enterococcus* assay mixture was placed on a 55° C. heat block. 40 µL of rehydration buffer were pipetted onto the heat-fixed sample on the glass coverslip. Rehydration Buffer was made by adding 0.15 mL of formamide and 50 µL of 10% Triton X-100 to 0.8 mL of nuclease free water. The coverslip was flipped over onto the glass slide so that all 5 spots were located beneath and within the heat-fixed sample area. The coverslip fit evenly onto the slide without hanging off any of the edges. The coverslip was not moved once it was in place.

Hybridization and Visualization

The slide and coverslip remained on the 55° C. heat block for 15 minutes. The slide was removed from the heat block and viewed on a fluorescence microscope equipped with a dual band pass filter using a 20× objective to evaluate localization of the PNA assay to within a 5.5 mm diameter circle. It was then evaluated using a 60× oil objective to interpret the results of the tests.

Interpretation

20× Objective:
  Red and green fluorescence are only seen within a 5.5 mm diameter circle around the initial point of application of the probe and
  quenchers—the polymer was able to keep the PNA assay localized Red and/or green fluorescence are seen beyond a 5.5 mm diameter circle around the initial point of application of the probe and
  quenchers—the polymer was unable to keep the PNA assay localized 60× Objective:
  Green fluorescence—successful hybridization of Efs
  Red fluorescence—successful hybridization of Efm

TABLE 1

Polymer Solutions Tested in Example 3

| Polymer | Manufacturer/Product Number | Mol. Weight | Viscosity (cP, 2% in H20 at 20 C.) | Amount of Polymer (g) | Amount of Water (ml) | Heat | Time |
|---|---|---|---|---|---|---|---|
| Poly(vinyl alcohol) | Sigma 363138 | 31k-50k | | 1 | 5 | 90° C. | 1 hr |
| Pullulan | Hayashibara | | | 0.5 | 2.5 | 55° C. | 1 hr |
| Polyvinylpyrrolidone | Sigma P5288 | 360k | | 0.5 | 1.25 | no | |
| Hydroxypropyl cellulose | Sigma 435007 | 80k | | 0.5 | 2 | no | |
| (Hydroxypropyl)methyl cellulose | Sigma H9262 | | 80-120 | 0.5 | 6 | no | |
| Polyacrylamide | Sigma 92560 | 5M-6M | | 0.5 | 9 | 55° C. | ON |
| Pectin, from apple | Sigma 76282 | | | 1 | 20 | 90° C. | 1 hr |
| Methyl cellulose | Sigma M0262 | 41k | 400 | 0.5 | 10 | no | |
| (Hydroxypropyl)methyl cellulose | Sigma H8384 | | 40-60 | 0.5 | 6.5 | | |
| D-(+)-Trehalose dihydrate | Sigma T9531 | | | 0.5 | 0.625 | no | |
| Dextran Sulphate | | 500k | | 20 | 41.5 | | |
| Poly(acrylic acid) | Sigma 306223 | 3M | | 0.5 | 15 | 55° C. | ON |
| Poly(acrylic acid) in 100 mM Tris Base | Sigma 306223 | 3M | | 0.5 | 50 | 55° C. | MX |
| Poly(acrylic acid) | Sigma 416002 | 250k | | | | | |

The pH of the Poly(acrylic acid), mol. wt. 3M, in water (0.5 g in 15 mL) is unknown. This was tested functionally with E/OE.
The pH of the Poly(acrylic acid), mol. wt. 3M, in 100 mM Tris, pH 9.4 (0.5 g in 30 mL) was between 5 and 6. This was not tested functionally.
The pH of the Poly(acrylic acid), mol. wt. 3M, in 100mM Tris Base (0.5 g in 50 mL) was between 8 and 9. This was tested functionally with E/OE.
Abbreviations:
hr = hour;
ON = overnight;
MX = mixing;
k = 1,000;
M = million

TABLE 2

Results from Polymer Solutions Tested

| Polymer | Localized | Background | Green Signal (Efs) | Red Signal (Efm) |
|---|---|---|---|---|
| Poly(vinyl alcohol), 98-99% hydrolyzed | Mostly Yes | Mostly Black | Great | Great |
| Pullulan | Yes | Black* | Great* | Great* |
| Polyvinylpyrrolidone | No | Very Green | Too Bright | Too Bright |
| Hydroxypropyl cellulose | Yes | Black* | Great | Great |
| (Hydroxypropyl)methyl cellulose, 40-60 cP | Mostly Yes | Black | Great | Great |
| Polyacrylamide | Yes | Slight Haze | Good | Good |
| Pectin, from apple | Yes | Black | Good | OK |
| Methyl cellulose | No/Yes | Black | Great | Great |
| (Hydroxypropyl)methyl cellulose, 80-120 cP | Yes | Slight Haze | Good | Good |
| D-(+)-Trehalose dihydrate | No | Hazy | Poor | Poor |
| Dextran Sulphate | Yes | Black | Great | Good |
| Poly(acrylic acid), mol. wt. 3M | No | Bright Red | Yellowish-Orange | OK |
| Poly(acrylic acid), mol. wt. 3M, in 100 mM Tris Base^ | No | Slight Haze | OK | OK |
| Poly(acrylic acid), mol. wt. 250k | | Bright Red | No | No |

*variable from well to well
^Poly(acrylic acid) had to be further diluted 2:3 before mixing it 1:1 with the 1:10 E/OE assay mixture Conclusions Several of the polymers tested could work well for this application. PVA, pullulan, hydroxypropyl cellulose, and (hydroxypropyl)methyl cellulose 40-60 cP (HPMC60) were all localized, produced bright red and green signals and dark backgrounds. Polyacrylamide, pectin, methyl cellulose, dextran sulphate, and (hydroxypropyl)methyl cellulose 80-120 cP, were acceptable, but using these conditions performed less well than those polymers previously indicated. For these specific embodiments, polyvinylpyrrolidone, poly(acrylic acid), and trehalose were either unable to localize the probes and quenchers or produce acceptable fluorescent signals and/or background and for these reasons were unacceptable.

Example 4 Stability

The stability of *Enterococcus* and *Staphylococcus* probes and quenchers were tested for stability at 37° C. and room temperature in solution together and separately and together in polymers cured onto slides.
Probe and Quencher Solutions
The PNA probes and quenchers for the *Enterococcus* assay mixture were mixed together 1:1 and stored at room temperature and 37° C. The probes and quenchers for the *Enterococcus* assay mixture were also stored separately at room temperature. The PNA probes and quenchers for the *Staphylococcus* assay mixture were mixed together 1:1 and stored at 37° C. The probes and quenchers for the *Staphylococcus* assay mixture were also stored separately at room temperature and 37° C.

Each of the *Enterococcus* and *Staphylococcus* assay mixtures were tested weekly. The assay mixtures were mixed 1:1 with a PVA solution. The *Enterococcus* assay mixture was diluted 1:10 before mixing with the PVA as a Polymer Solution. Five 0.5 µL drops of a single probe and quencher polymer solution were pipetted onto a 25 mm×75 mm×1 mm glass microscope slide. The solution was spread into 3.5 mm diameter circles. The five circles were arranged in an equidistant, circular pattern within a 19 mm circle. The circles were spaced 4.44 mm apart. The slides for each assay mixture were cured for an hour in a 70° C. oven.
*Enterococcus* Slides
PNA probes and quenchers for the *Enterococcus* assay mixture were mixed 1:1 with PVA (1 g and 5 mL of water), pullulan (1 g and 5 mL of water), and HPMC60 (0.5 g and 6.5 mL of water) solutions. Five 0.5 µL drops of a single probe and quencher polymer solution were pipetted onto 25 mm×75 mm×1 mm glass microscope slides. The solution was spread into 3.5 mm diameter circles. The five circles were arranged in an equidistant, circular pattern within a 19 mm circle. The circles were spaced 4.44 mm apart. The slides were cured for an hour in a 70° C. oven and stored exposed to ambient conditions at room temperature and 37° C. non-humidified incubator. The slides stored at 37° C. were tested weekly. The slides stored at room temperature were tested every other week.
*Staphylococcus* Slides
PNA probes and quenchers for the *Staphylococcus* assay mixture were mixed 1:1 with a PVA as a Polymer Solution (1 g and 5 mL of water). Five 0.5 µL drops of the probe and quencher polymer solution were pipetted onto 25 mm×75 mm×1 mm glass microscope slides. The solution was spread into 3.5 mm diameter circles. The five circles were arranged in an equidistant, circular pattern within a 19 mm circle. The circles were spaced 4.44 mm apart. The slides were cured for an hour in a 70° C. oven and stored exposed to ambient conditions at room temperature and 37° C. non-humidified incubator. The slides were tested weekly.
Heat-Fixed Sample
10 µL of blood culture containing Efs and Efm for the *Enterococcus* assay mixture or *Staphylococcus aureus* (SA) and *epidermidis* (SE) for the *Staphylococcus* assay mixture were pipetted onto a 24 mm×50 mm glass coverslip on a 55° C. heat block. One drop of QuickFix-1 was immediately mixed into the blood culture and spread into a 22 mm circle. The mixture was allowed to dry completely. 100 µL of QuickFix-2 was pipetted evenly over the entire circle and allowed to dry completely.
Rehydration
The glass slides with the assay mixtures were placed on a 55° C. heat block. 40 µL of rehydration buffer were pipetted onto the heat-fixed sample on the glass coverslips. Rehydration Buffer was made by adding 0.15 mL of formamide and 50 µL of 10% Triton X-100 to 0.8 mL of nuclease free water. The coverslips were flipped over onto the glass slides so that all 5 spots were located beneath and within the heat-fixed sample area. The coverslip fit evenly onto the slide without hanging off any of the edges. The coverslip was not moved once it was in place.
Hybridization and Visualization
The slides and coverslips remained on the 55° C. heat block for 15 minutes. The slide was removed from the heat block and viewed on a fluorescence microscope equipped with a dual band pass filter using a 60× oil objective to interpret the results of the tests.
Interpretation
*Enterococcus* assay:
　Green fluorescence—hybridization of Efs
　Red fluorescence—hybridization of Efm
*Staphylococcus* assay:
　Green fluorescence—hybridization of SA
　Red fluorescence—hybridization of SE
Signal Intensity:
　3+=Bright, sparkling fluorescence
　3=Bright fluorescence
　2=Fluorescent, but not bright
　1=Very dim fluorescence
　0=No fluorescence visible
Stable: Signal intensity remains the same or nearly the same with time
Unstable: Signal intensity decreases with time
Results

TABLE 3

*Enterococcus* slides stored at 37° C.

| Week | PVA | Pullulan |
|---|---|---|
| 1 | 3+ red and green signal | 3+ red and green signal |
| 2 | 3+ red and green signal | 3+ red and green signal |
| 3 | 3+ red and green signal | 3+ red and green signal |
| 4 | 3+ red and green signal | 3+ red and green signal |
| 5 | 3+ red and green signal | 3+ red and green signal |
| 6 | 3+ red and green signal | 3+ red and green signal |
| 7 | 3+ red and green signal | 3+ red and green signal |
| 8 | 3+ red and green signal | 3+ red and green signal |
| 9 | 3+ red and green signal | 3+ red and green signal |
| 10 | 3+ red and green signal | 3+ red and green signal |
| 11 | 3+ red and green signal | 3+ red and green signal |
| 12 | 3+ red and green signal | 3+ red and green signal |

TABLE 4

*Enterococcus* slides stored at room temperature

| Week | PVA | Pullulan | HPMC60 |
|---|---|---|---|
| 2 | 3+ red & green signal | 3+ red & green signal | 3+ red & green signal |
| 4 | 3+ red & green signal | 3+ red & green signal | 3+ red & green signal |
| 6 | 3+ red & green signal | 3+ red & green signal | 3+ red & green signal |

TABLE 4-continued

Enterococcus slides stored at room temperature

| Week | PVA | Pullulan | HPMC60 |
|------|-----|----------|--------|
| 8 | 3+ red & green signal | 3+ red & green signal | 3+ red & green signal |
| 10 | 3+ red & green signal | 3+ red & green signal | 3+ red & green signal |
| 12 | 3+ red & green signal | 3+ red & green signal | 3+ red & green signal |

TABLE 5

Staphylococcus slides and Enterococcus and Staphylococcus probes and quenchers at room temperature and 37° C.

| | Staph Slides | | 4X Staphylococcus Assay mixtures | | | | | | 4X Enterococcus Assay mixture | | | | | | |
|---|---|---|---|---|---|---|---|---|---|---|---|---|---|---|---|
| | | | Probe & Quencher Together | | Probe & Quencher Separate | | Probe & Quencher Separate | | Probe & Quencher Together | | Probe & Quencher Together | | Probe & Quencher Separate | | |
| | RT | 37° C. | 37° C. | | 37° C. | | RT | | 37° C. | | RT | | RT | | |
| Week | G | R | G | R | G | R | G | R | G | R | G | R | G | R | G | R |
| 1^ | 3* | 3+ | 3* | 3+ | 3* | 3+ | 3* | 3+ | 3* | 3+ | 3+ | 3+ | 3+ | 3+ | 3+ | 3+ |
| 2^ | 3* | 3+ | 3* | 3+ | 3* | 3+ | 3* | 3+ | 3* | 3+ | 3+ | 3+ | 3+ | 3+ | 3+ | 3+ |
| 3 | 3* | 3+ | 3* | 3+ | 1− | 1+ | 2* | 3 | 2*¥ | 2+¥ | 3 | 0 | 2 | 0 | 3+ | 3+ |
| 4^ | 3* | 3+ | 3* | 3 | 3* | 3+ | 3* | 3+ | 2+* | 2+ | 3 | 2+* | 3+ | 3* | 3 | 2+ |
| 5 | 3* | 3+ | 3* | 3+ | 0 | 2− | 1+ | 2− | 3* | 3+ | 2 | 1+ | 2− | 0 | 3+ | 3+ |

*signal is variable
^the probes and quenchers were vortexed before adding them to the polymer on these 3 dates, but not the other dates
¥this was a new assay mixture made on Aug. 15, 2012; it was vortexed and remixed into polymer and retested--green 3* and red 3+
G = green fluorescent signal
R = red fluorescent signal Conclusions PNA probes and quenchers are unstable when mixed together in solution. PNA probes are unstable in solution stored separately from the quenchers. PNA probes and quenchers mixed together in a polymer solution and cured onto glass slides are stable for several weeks.

Example 5 Spin Coating

A Probe and Quencher Polymer Solution was spotted into a spin coated polymer film.

Probe and Quencher Polymer Solution

The Probe and Quencher Polymer Solution was prepared by mixing PNA Staphylococcus assay mixture 1:1 with a polymer solution. The probes and quenchers for the PNA Staphylococcus assay mixture were diluted separately in a buffer containing 82.2 mM HEPBS, 0.1% sodium pyrophosphate decahydrate, 10 mM sodium chloride, 5 mM EDTA, 0.25% PEG, 15% formamide, and 0.5% Triton X-100 and remained separate until preparation of the Probe and Quencher Polymer Solution. The Polymer Solution was prepared by adding 1 g of PVA to 5 mL of nuclease free water and heating in a 95° C. water bath for one hour to dissolve completely.

Slides 0.5 g of PVA was added to 5 mL of nuclease free water and heated in a 95° C. water bath for one hour to dissolve completely. 75 µL of formamide was added to 0.925 mL of the PVA solution. 100 µl of the PVA/formamide solution was pipetted into the center of a 25 mm×75 mm×1 mm glass microscope slide in a custom holder attached to the spindle of an IEC HN centrifuge (International Equipment Co., Needham, Mass.). The slide was spun at approximately 4,650 rpm for 15 seconds. 0.5 µL of the Probe and Quencher Polymer Solution was immediately pipetted into the wet PVA film in four separate locations. The solution spread in a radial fashion. The slide was then cured for an hour in a 70° C. oven.

Heat-Fixed Sample

10 µL of blood culture containing Staphylococcus aureus (SA) and Staphylococcus epidermidis (SE) were pipetted onto a 24 mm×50 mm glass coverslip on a 55° C. heat block. One drop of QuickFix-1 was immediately mixed into the blood culture and spread into a 22 mm circle. The mixture was allowed to dry completely. 100 µL of QuickFix-2 were pipetted evenly over the entire circle and allowed to dry completely.

Rehydration

The glass slide is placed on a 55° C. heat block. 40 µL of Rehydration Buffer was pipetted onto the heat-fixed sample on the glass coverslip. Rehydration Buffer is made by adding 0.15 mL of formamide and 50 µL of 10% Triton X-100 to 0.8 mL of nuclease free water. The coverslip was flipped over onto the glass slide so that all four spots were located beneath and within the heat-fixed sample area. The coverslip fit evenly onto the slide without hanging off any of the edges. The coverslip was not moved once it was in place.

Hybridization and Visualization

Hybridization of the probes and target, if present, began after rehydration while the slide and coverslip remained on the 55° C. heat block for 15 minutes. Once the slide was removed from the heat block, the quenchers hybridized to any unbound probe. The slide was viewed on a fluorescence microscope equipped with a dual band pass filter using a 20× objective to evaluate localization of the PNA assay. It is then evaluated using a 60× oil objective to interpret the results of the tests.

Interpretation

20× Objective:

- Red and green fluorescence are only seen within the area in which the probe and quencher polymer solution spread when applied to the film—the PNA Staphylococcus assay was localized
- Red and/or green fluorescence are seen beyond the area in which the probe and quencher polymer solution spread when applied to the film—the PNA Staphylococcus assay was not localized 60× Objective:
    Green fluorescence—successful hybridization of SA
    Red fluorescence—successful hybridization of SE
Conclusion PNA probes and quenchers in a polymer solution were localized when embedded and cured in a polymer film. SA and SE were successfully hybridized when the PNA *Staphylococcus* assay mixture was mixed into a Polymer Solution and embedded and cured in a polymer film.

Example 6 Reduced Localization with In-Solution Samples

In initial experiments directed to the testing of PNA embedded in polymer matrix (discussed above), the blood culture samples were heat-fixed to the coverslip; the polymer spots and sample were rehydrated simultaneously with Rehydration Buffer; and the fluorescent signal from the organisms post hybridization was localized. However, when we moved from using a sample that was heat-fixed on the coverslip to a sample that remained in solution with AIOBA which rehydrates the polymer spots, we found that the signal was no longer localized (hybridized organisms were observed outside the reagent zone). Therefore, it was logical to examine the differences between the two systems and attempt to optimize the system to ensure localization when prefabricated slides were used in combination with patient samples. Below is a brief description of some representative experiments formed and results obtained.

Fixed-Sample Conditions (Localized):
    PVA (Molecular Weight 31,000-50,000 or "mw 31-50 k")
        0.5 g plus 5 ml H$_2$O
    0.5 µl PVA with PNA spread in 3.5 mm circles on slide
    Cured for 1 hour at 70° C.
    10 µl blood culture+1 drop QuickFix-1 spread into a 22 mm circle on 24×50 mm coverslip on a 55° C. heat block
    100 µl QuickFix-2 over the entire circle on 55° C. heat block
    40 µl of Rehydration Buffer on coverslip and flipped onto slide with PVA spots Initial In-Solution Conditions (not Localized):
    PVA (mw 31-50 k) 0.5 g plus 5 ml H$_2$O
    0.5 µl PVA with PNA spread in 3.5 mm circles on slide
    Cured for 1 hour at 70° C.
    10 µl heated and cooled blood culture with 30 µl AIO Buffer B onto 24×50 mm coverslip
    Flipped onto slide Example 7 Polymers/Conditions that Did not Localize In-Solution Samples Below are brief descriptions of the different potential solutions we tried that were not successful in localizing the fluorescent signals.

1. Increasing the Amount of PVA in the Polymer Spot:

We increased the amount of PVA from 0.5 mg to 0.75 g plus 5 ml H$_2$O. Localization can be achieved with more PVA, but at that point it also prevents the probe from getting to the organism, and there is too little signal.

2. Using Higher Molecular Weight PVA:

85,000-124,000 molecular weight (mol. wt.) PVA and 146,000-186,000 mol. wt. PVA in place of the 31,000-50,000 mol. wt. PVA. The higher molecular weight PVA polymers were also not localized.

3. Using Polymers Other than PVA:

Pectin, pullulan, Dextran sulfate (DexSO$_4$), polyacrylamide, hydroxypropyl cellulose, hydroxpropylmethyl cellulose (80-120 cP), polyethylene oxide (PEO), or poly(n-isopropylacrylamide) in place of PVA or PEO mixed with PVA. Although the signal was localized with fixed samples, it was not with in-solution samples.

4. Stasis Prior to Rehydration:

Flipped the coverslip with the sample and AlO Buffer B onto a room temperature slide rather than on the heat block. The signal was not localized, and the signal and background were terrible.

5. Altering the Buffer:

Simple Buffer (see below), a buffer more like Rehydration Buffer, in place of AlO Buffer B. Although localization was improved, perhaps because of the reduction in the amount of detergent, it was not completely localized.

| Simple Buffer | |
| --- | --- |
| Formamide | 15% |
| Triton X-100 | 0.5% |
| MgCl$_2$ | 37.5 mM |

Original AlO Buffer (see below) in place of AlO Buffer B. Although localization was improved, again perhaps because of the reduction in the amount of detergent, it was not completely localized.

| Original AlO Buffer | |
| --- | --- |
| HEPBS | 83 mM |
| NaCl | 22.8 mM |
| EDTA | 5.00 mM |
| PEG | 0.25% |
| Formamide | 15% |
| Triton X-100 | 0.5% |
| MgCl2 | 56.2 mM |
| Tris pH 9.0 | 90 mM |
| CuSO4 | 4.5 mM |

6. Rinsing PVA Spots:

Rinsed cured PNA polymer spots with dimethyl formamide or ethanol to remove PNA on the surface of the spot. The signal was not localized.

7. Spin Coating:

Spin coated slides with 250 µl of 0.5 g PVA plus 5 ml of 7.5% formamide and placed the PNA polymer spots on top of the spin coating. Although, the sample looked very flat, the lack of localization was even worse with the spin coating.

Spin coated slides with 150 µl of 600 k PEO in ethanol (25 mg/ml) with cured PNA polymer spots below the spin coating. The signal was not localized, and it looked bad.

8. Capping with Polymer in Aqueous Solvent:

Capped with 1 µl of 0.5 g PVA plus 5 ml of 7.5% formamide with and without pre-treatment with ethanol. The signal was localized only if you were able to place the cap without disturbing the bottom PVA layer, but this was very difficult because the PVA quickly begins to rehydrate. If the bottom PVA layer was disturbed, which it most often was, the signal was not localized.

Example 8 Experiments Showing Polyethylene Oxide (PEO) Caps Over Matrix Zones Localize In-Solution Samples Slide Preparation Five 5.5 mm circles spaced evenly within the circumference of a 22 mm circle were drawn on the back side of a 25×75 mm plain glass slide with a black marker. 5 g of PVA (mw 31-50 k) was dissolved in 5 ml of water and mixed 1:1 with a PNA assay mixture. 0.5 µl of the PVA with PNA was spread in 3.5 mm circles within each of the five 5.5 mm circles on the front side of the slide. The polymer spots were cured in a 70° C. oven for 1 hour. PEO (600 k mol. wt.) was dissolved in ethanol at 55° C. 1 µl of PEO was spread in each of the 5.5 mm circles over the cured PVA spot to form capped polymer spots. The capped polymer spots were cured again for 1 hour at 70° C.

Sample Preparation 1 ml of sterile blood culture was inoculated with bacteria or yeast and incubated at 37° C. for 1.5 to 4 hours to produce Mock Blood Culture. 200 µl of Mock Blood Culture in a 2 ml, round-bottom, microcentrifuge tube were heat treated at 80° C. for two minutes in a dry heat block and cooled to room temperature. 25 µl of cooled Mock Blood Culture was mixed with 75 µl of AlO Buffer to produce Mock Blood Culture/Buffer Mixture.

Hybridization and Interpretation

The capped polymer slide was placed on a 55° C. heat block and a 24×50 mm coverslip was place in an AdvanDx QuickFISH Mixing Station. 40 µl of Mock Blood Culture/Buffer Mixture was pipetted across the coverslip, and the coverslip was flipped onto the slide. The slide and coverslip remained on the heat block undisturbed for 15 minutes. The slide was viewed at 20× and 60× oil using the QuickFISH dual band filter. The black marker is visible as fluorescent red. If fluorescent organisms were only seen within the red fluorescent circle, then it was considered localized.

Below are the Conditions Tested, and their Results:

|  | PNA Assay mixture | Primary Polymer with PNA | Secondary Polymer (cap) Concentration | Organisms Tested | Results |
|---|---|---|---|---|---|
| Experiment 1 | GNR | PVA | PEO, 12.5 mg/ml | EC KP PA | not localized |
|  | GNR | PVA | PEO, 25 mg/ml | EC KP PA | localized, signal brighter and flatter |
|  | GNR | PAA | PEO, 12.5 mg/ml | EC KP PA | not localized |
|  | GNR | PAA | PEO, 25 mg/ml | EC KP PA | localized, signal brighter and flatter |
|  | GNR | PVA | no cap | EC KP PA | not localized |
|  | GNR | PVA | no cap | EC KP PA | not localized |
|  | GNR | PAA | no cap | EC KP PA | not localized |
|  | GNR | PAA | no cap | EC KP PA | not localized |
| Experiment 2 | Sa/Se | PVA | PEO, 25 mg/ml | SA SE | not localized[1] |
|  | E/OE | PVA | PEO, 25 mg/ml | Efs Efm | localized |
|  | GNR | PVA | PEO, 25 mg/ml | EC KP PA | localized |
|  | Sa/Se | PVA | no cap | SA SE | Localized[1] |
|  | E/OE | PVA | no cap | Efs Efm | not localized |
|  | GNR | PVA | no cap | EC KP PA | not localized |
| Experiment 3 | GNR | PVA | PEO, 25 mg/ml | EC KP PA | localized |
|  | Sa/Se | PVA | PEO, 25 mg/ml | SA SE | localized |
|  | Sa/Se | PVA | PEO, 25 mg/ml | SA SE | localized |
|  | 0.2X Sa/Se | PVA | PEO, 26 mg/ml | SA SE | localized, reduced signal |
|  | Yeast | PVA | PEO, 25 mg/ml | CA CP CG | localized |
|  | GNR | PVA | no cap | EC KP PA | not localized |
|  | Sa/Se | PVA | no cap | SA SE | not localized |
|  | 0.2X Sa/Se | PVA | no cap | SA SE | not localized, reduced signal |
|  | Yeast | PVA | no cap | CA CP CG | not localized |

[1]The labeling on these 2 slides may have been inadvertently switched, results from repeat testing were different and in line with the other experiments.
Abbreviations Used In The Table:
GNR = Gram Negative Rods;
Sa/Se = *S. aureus*/*S. epidermidis*;
E/OE = *E. faecalis*/Other *Enterococci*;
PVA = Polyvinyl alcohol;
PAA = Polyacrylamide;
PEO = Polyethylene oxide Conclusions Capping the PNA polymer spots with 600 k mol. wt. PEO at 25 mg/ml not only localizes signal within an in-solution sample, but it makes the sample appear flatter and the signal brighter. PNA polymer spots with less or no PEO do not provide localized signal with an in-solution sample.

Example 9 Different PEO Concentrations/Molecular Weights Tested

Below are brief descriptions of the performance of various PEO concentrations and molecular weights.

100K PEO

1 µl caps of 100,000 molecular weight PEO (100 k PEO) in ethanol at 25 mg/ml do not localize fluorescent signal in an in-solution sample. 75 mg and 150 mg/ml of 100 k PEO in ethanol was too green fluorescent on its own to be useful.

300 k PEO

1 μl caps of 300,000 molecular weight (300 k PEO) in ethanol at 25 mg/ml do localize fluorescent signal in an in-solution sample, are less green fluorescent, but does not make the sample look as flat as 600 k PEO.

600 k PEO

1 μl caps of 600,000 molecular weight (600 k PEO) in ethanol, dichloroethane, or chloroform at 25 mg/ml does localize fluorescent signal in an in-solution sample, make the sample appear flat, and the signal brighter. The chloroform solution was difficult to spread evenly.

1 μl caps of 600 k PEO in chloroform at 22.5 mg/ml does localize fluorescent signal in an in-solution sample, but the sample does not look as flat and the fluorescent signal was not as bright as the 25 mg/ml solution. The 22.5 mg/ml solution, however, was easier to spread evenly than the 25 mg/ml solution.

1 μl caps of 600 k PEO in chloroform at 20 mg/ml does not localize fluorescent signal in an in-solution sample; it does not look flat, but it was easy to spread evenly.

1 μl caps of 600 k PEO in ethanol at 12.5 mg/ml does not localize fluorescent signal in an in-solution sample.

Solvents Tested

Below are brief descriptions of the behavior of PEO dissolved in various solvents.

- PEO in ethanol performed well, but did not stay in solution at room temperature.
- Dimethyl formamide, n-methylpyrrolidone were not acceptable solvents for PEO.
- PEO in methylene chloride was clear and in solution at room temperature, but the assays did not look as good as when ethanol was used.
- PEO in acetonitrile was hazy in solution at room temperature, and the assays did not look as good as when ethanol was used.
- PEO in isopropanol, xylenes, or tetrachloroethylene did not stay in solution at room temperature.
- The assays looked good with PEO in chloroform; the PEO stayed in solution at room temperature, but it was difficult to spread evenly and negatively affected signal uniformity.
- The assays looked good with PEO in dichloroethane; the PEO stayed in solution at room temperature, and it spread relatively easily.

Example 10 An Exemplary Embodiment

Slide Preparation

Five 7.5 mm circles were spaced evenly within the circumference of a 22 mm circle drawn on the back side of a 25×75 mm plain glass slide with a black marker. 5 g of PVA (mw 31-50 k) was dissolved in 5 ml of water and mixed 1:1 with a PNA assay mixture as described in Example 1. 0.5 μl of the PVA with PNA from the PNA assay mixture was spread in 5.5 mm circles within each of the five 7.5 mm circles on the front side of the slide. The polymer spots were cured in a 70° C. oven for 1 hour. PEO (600 k mol. wt.) was dissolved in dichloroethane to prepare a PEO Stock. 1 μl of PEO Stock was spread in each of the 7.5 mm circles over the cured PVA spot to produce Capped Polymer Spots. The Capped Polymer Spots were cured again for 1 hour at 70° C. A 24×40 mm coverslip was applied to the top side of the glass slide.

Sample Preparation 1 ml of sterile blood culture inoculated with bacteria or yeast was incubated at 37° C. for 1.5 to 4 hours to produce Mock Blood Culture. 200 μl of Mock Blood Culture in a 2 ml, round-bottom, microcentrifuge tube was heat treated at 80° C. for two minutes in a dry heat block and cooled to room temperature. 50 μl of cooled Mock Blood Culture was mixed with 50 μl of AlO Buffer B to product a Blood Culture/Buffer Mixture.

| All-In-One Buffer B | |
|---|---|
| NaCl | 0.013M |
| EDTA | 0.007M |
| PEG, 35K | 0.63% |
| Formamide | 37.81% |
| Triton X-100 | 2.1% |
| MgCl2 | 0.075M |
| Tris, pH 9 | 0.18M |
| CuSO4 | 0.0045M |

Hybridization and Interpretation

A capped polymer slide was placed on a 55° C. heat block. 50 μl of Blood Culture/Buffer Mixture was pipetted on the edge of the coverslip and allowed to fill the space beneath the coverslip by capillary action. The slide and coverslip remain on the heat block undisturbed for 15 minutes. The slide is viewed at 20× and 60× oil using the QuickFISH dual band filter.

8. References

All of which are incorporated by reference in their entirety for all purposes

US Patent and Published Patent Applications

1. U.S. Pat. No. 4,219,334 to Schluter et al., issued Aug. 26, 1980
2. U.S. Pat. No. 5,397,711 to Finckh, Peter, issued Mar. 14, 1995
3. U.S. Pat. No. 5,403,706 to Wilk et al., issued Apr. 4, 1995
4. U.S. Pat. No. 5,726,064 to Robinson et al., issued Mar. 10, 1998
5. U.S. Pat. No. 6,045,753 to Loewy et al., issued Apr. 4, 2000
6. U.S. Pat. No. 6,309,893 to Deeley et al., issued Oct. 30, 2001
7. U.S. Pat. No. 6,355,421 to Coull et al., issued Mar. 12, 2002
8. U.S. Pat. No. 6,361,942 to Coull et al., issued Mar. 26, 2002
9. U.S. Pat. No. 6,607,889 to Coull et al., issued Aug. 19, 2003
10. U.S. Pat. No. 6,649,349 to Gildea et al, issued Nov. 8, 2003
11. U.S. Pat. No. 6,905,824 to Rigby et al., issued Jun. 14, 2005
12. US Published Patent Application No. US 2009/0325263 A1 to Ponaka et al. published on Dec. 31, 2009

Scientific Publications

1. Janson and During, "Peptide Nucleic Acids, Morpholinos and Related Antisense Biomolecules", Chapter 7, "Chemistry of Locked Nucleic Acids (LNA)", Springer Science & Business, 2006
2. Vilaivan et al., "Hybridization of Pyrrolidinyl Peptide Nucleic Acids and DNA: Selectivity, Base-Pairing Specificity and Direction of Binding", Organic Letters, 8(9): 1897-1900 (2006) While the present teachings are described in conjunction with various embodiments, it is not intended that the present teachings be limited to such embodiments. On the contrary, the present teachings encompass various alternatives, modifications and equivalents, as will be appreciated by those of skill in the art.

We claim:

1. A composition comprising a matrix zone and a polymer cap disposed on the matrix zone; wherein the matrix zone comprises:
   i) at least one hybridization probe comprising a linked fluorescent label;
   ii) at least one hybridization probe comprising a linked quencher moiety; and
   iii) at least one matrix-forming prolonged-dissolution hydrophilic polymer;
      wherein said matrix zone is a gel, semi-solid or solid;
      wherein said matrix-forming prolonged-dissolution hydrophilic polymer is selected from the group consisting of: multi-subunit sugar copolymers, pullulan, methyl cellulose, carboxymethyl cellulose, carboxyethyl cellulose, carboxypropyl cellulose, hydroxyethyl cellulose, hydroxypropyl cellulose, hydroxypropyl methyl cellulose, polyvinylalcohol(s), polyacrylamide(s), polyethyleneimines(s), pectin(s) or mixtures of any two or more of the forgoing; wherein the matrix-forming prolonged-dissolution hydrophilic polymer localize the hybridization probe;
      wherein the polymer cap comprises polyethylene oxide (PEO) with molecular weight of 300-600 k g/mol.

2. The composition of claim 1, wherein one or both of: i) said at least one hybridization probe comprising a linked fluorescent label and ii) said at least one hybridization probe comprising a linked quencher moiety, is a peptide nucleic acid probe.

3. The composition of claim 1, wherein said composition is disposed on a substrate.

4. The composition of claim 1, wherein the polymer cap is soluble in ethanol, acetonitrile, methylene chloride, chloroform, benzene or dichloroethane.

5. The composition of claim 1, further comprising a buffer, residual water, and/or a detergent.

6. An assay device comprising:
   i) a first substrate comprising a first surface;
   ii) at least two matrix zones disposed on said first surface of said first substrate wherein at least one of said at least two matrix zones comprises: a) at least one hybridization probe comprising a linked fluorescent label; b) at least one hybridization probe comprising a linked quencher moiety; and c) at least one matrix-forming prolonged-dissolution hydrophilic polymer, wherein each matrix zone is a gel, semi-solid or solid; and
   iii) a polymer cap disposed on the substrate and over each matrix zone; wherein each matrix zone is located between the polymer cap and the substrate;
      wherein said matrix-forming prolonged-dissolution hydrophilic polymer is selected from the group consisting of: multi-subunit sugar copolymers, pullulan, methyl cellulose, carboxymethyl cellulose, carboxyethyl cellulose, carboxypropyl cellulose, hydroxyethyl cellulose, hydroxypropyl cellulose, hydroxypropyl methyl cellulose, polyvinylalcohol(s), polyacrylamide(s), polyethyleneimines(s), pectin(s) or mixtures of any two or more of the forgoing; wherein the matrix-forming prolonged-dissolution hydrophilic polymer localize the hybridization probe;
      wherein the polymer cap comprises polyethylene oxide (PEO) with molecular weight of 300-600 k g/mol.

7. An assay device comprising:
   i) a substrate comprising a surface;
   ii) a matrix film disposed on said surface of said substrate comprising a matrix-forming prolonged-dissolution hydrophilic polymer; wherein said matrix-forming prolonged-dissolution hydrophilic polymer is selected from the group consisting of: multi-subunit sugar copolymers, pullulan, methyl cellulose, carboxymethyl cellulose, carboxyethyl cellulose, carboxypropyl cellulose, hydroxyethyl cellulose, hydroxypropyl cellulose, hydroxypropyl methyl cellulose, polyvinylalcohol(s), polyacrylamide(s), polyethyleneimines(s), pectin(s) or mixtures of any two or more of the forgoing; wherein the matrix-forming prolonged-dissolution hydrophilic polymer localize the hybridization probe;
   iii) at least two reagent zones disposed within the matrix film, wherein the reagent zones comprise at least one hybridization probe comprising a linked fluorescent label and at least one hybridization probe comprising a linked quencher moiety; and
   iv) a polymer cap disposed over the matrix film; wherein the polymer cap comprises polyethylene oxide (PEO) with molecular weight of 300-600 k g/mol.

8. The assay device of claim 6, further comprises a second substrate comprising a second surface.

9. The assay device of claim 8, further comprises a sample disposed on said second surface.

10. The assay device of claim 6, wherein said hybridization probe comprising a linked fluorescent label at said at least one of said at least two matrix zones is different as compared with the hybridization probes at a second matrix zone of said at least two matrix zones.

11. The assay device of claim 6, wherein, for one or more of said matrix zones, at least one hybridization probe is a peptide nucleic acid probe.

12. The assay device of claim 6, wherein said surface of said substrate comprises from 2 to 20 matrix zones.

13. The assay device of claim 6, wherein at least one matrix zone further comprises a buffer, residual water, and/or a detergent.

14. The assay device of claim 6, wherein the polymer cap is soluble in ethanol, acetonitrile, methylene chloride, chloroform, benzene or dichloroethane.

15. The assay device of claim 6, wherein said first surface of said first substrate is flat or substantially flat.

16. The assay device of claim 6, wherein said first substrate is transparent.

17. The assay device of claim 8, wherein said second surface of said second substrate is flat or substantially flat.

18. The assay device of claim 8, wherein said second substrate is transparent.

19. The assay device of claim 8, wherein the first surface of the first substrate and the second surface of the second substrate are separated by a narrow gap.

20. The assay device of claim 8, further comprising a liquid disposed between said first surface of said first substrate and said second surface of said second substrate.

21. The assay device of claim 20, wherein said liquid further comprises a sample.

22. The assay device claim 20, wherein said liquid is water or an aqueous solution that may optionally comprise detergent and/or buffer.

23. A method comprising:
A) providing the assay device of claim 8;
B) disposing an aqueous liquid between said first surface of said first substrate and said second surface of said second substrate such that said first surface and said second surface are in liquid communication; wherein the liquid comprises a sample.

24. The method of claim 23 further comprising: C) waiting for a period of time sufficient for said matrix-forming prolonged-dissolution hydrophilic polymer to rehydrate and sufficient for a) said at least one hybridization probe comprising a linked fluorescent label and b) said at least one hybridization probe comprising a linked quencher moiety present at said matrix zone to interact with each other and with said sample.

25. The method of claim 24 further comprising: D) determining one or more conditions of interest of said sample based, at least in part, on how: a) said at least one hybridization probe comprising a linked fluorescent label; and b) said at least one hybridization probe comprising a linked quencher moiety interact with each other and with said sample at one or more of said at least two matrix zones.

26. The method of claim 23, wherein the sample is blood culture, bronchoalveolar lavage, urine or other bodily fluids.

27. The composition of claim 1, wherein the matrix-forming prolonged-dissolution hydrophilic polymer is selected from the group consisting of pullulan, methyl cellulose, hydroxypropyl cellulose, hydroxypropyl methyl cellulose, polyvinylalcohol(s), polyacrylamide(s), pectin(s), dextran sulphate, or mixtures of any two or more of the forgoing.

28. The composition of claim 1, wherein the matrix-forming prolonged-dissolution hydrophilic polymer is selected from the group consisting of pullulan, hydroxypropyl cellulose, hydroxypropyl methyl cellulose, polyvinylalcohol(s), or mixtures of any two or more of the forgoing.

29. The composition of claim 1, wherein the matrix-forming prolonged-dissolution hydrophilic polymer is polyvinylalcohol.

30. The composition of claim 1, wherein the matrix-forming prolonged-dissolution hydrophilic polymer is polyvinylalcohol with molecular weight of 31-50 k g/mol.

31. The composition of claim 1, wherein the polymer cap comprises polyethylene oxide (PEO) with molecular weight of 600 k g/mol.

32. The assay device of claim 6, wherein the polymer cap comprises polyethylene oxide (PEO) with molecular weight of 600 k g/mol.

33. The assay device of claim 6, wherein the matrix-forming prolonged-dissolution hydrophilic polymer is polyvinylalcohol.

34. The assay device of claim 6, wherein the matrix-forming prolonged-dissolution hydrophilic polymer is polyvinylalcohol with molecular weight of 31-50 k g/mol.

* * * * *